United States Patent
Templeton et al.

(10) Patent No.: US 6,306,620 B1
(45) Date of Patent: Oct. 23, 2001

(54) METHOD FOR ASSESSING THE VIABILITY OF PLANT TISSUE USING A COLORIMETRIC REAGENT

(76) Inventors: Colin William George Templeton, 53 Riverview Ave., Sault Ste. Marie, Ontario (CA), P6A 3X8; Stephen John Colombo, 141 Prineton Dive, Sault Ste. Marie (CA), P6B 5T4

( * ) Notice: Subject to any disclaimer, the term of this patent is extended or adjusted under 35 U.S.C. 154(b) by 0 days.

(21) Appl. No.: 08/648,505

(22) Filed: May 15, 1996

Related U.S. Application Data

(63) Continuation-in-part of application No. 08/440,950, filed on May 15, 1995, now abandoned.

(51) Int. Cl.$^7$ .................................................. C12Q 1/02
(52) U.S. Cl. .............................. 435/29; 422/79; 422/83
(58) Field of Search ................................ 435/29; 422/50, 422/79, 83, 85, 86, 87; 436/130, 132, 164

(56) References Cited

U.S. PATENT DOCUMENTS

| | | | |
|---|---|---|---|
| 3,388,975 | * 6/1968 | Wallace | 23/254 |
| 4,159,304 | 6/1979 | Shono | 422/104 |
| 4,389,372 | 6/1983 | Lalin | 422/88 |
| 5,136,805 | 8/1992 | Mookherjee | 47/69 |
| 5,263,359 | 11/1993 | Mookherjee et al. | 73/23.34 |
| 5,269,169 | 12/1993 | Trenkle et al. | 73/23.34 |
| 5,447,688 | * 9/1995 | Moore | 422/56 |

FOREIGN PATENT DOCUMENTS

| | | |
|---|---|---|
| 1 156 253 | 10/1963 | (DE) . |
| 0 174 289 A1 | 3/1986 | (EP) . |
| 0 364 952 A2 | 4/1990 | (EP) . |

OTHER PUBLICATIONS

Mattsson, A., New Forests 13:227–252, 1997.
Hawkins and Binder, Target Seedling Syumposium, State of the Art Seedling Stock Quality Tests Based on Seedling Physiology, pp. 91–121, 1990.
Rook, D.A. New Zealand Journal of Forestry Science, vol. 10, Preface, 1980.
Kimmerer T., Ethylene, Ethane, Acetaldehyde, and Ethanol Production by Plants Under Stress, Plant Physiol, vol. 69 840–847, 1982.*
Johnson J., Assessing Freeze Damage in Loblolly Pine Seedlings: A Comparison of Ethane Production to Electrolyte Leakage, New Forests 2:65–72, 1988.*
Bressan R., Emission of Ethylene and Ethane by Leaf Tissue Exposed to Injurious Concentrations of Sulfur Dioxide or Bisulfite Ion, Plant Physiol 63:924–930, 1979.*
Pratt H., Physiological Roles of Ethylene in Plants, Ann Rev Plant Pnysiol 20:541–584, 1969.*
Kimmerer et al., Chemical Abstracts, Abstract No. 178051n, 96:428, 1982.
Shamalia et al., J. of Food Sci., 57:1168–1172, 1992.
Woodstock et al., Chemical Abstracts, Abstract No. 153551, 94:370, 1981.
Kimmerer and Kozlowski, Plant Physiol. 69:840–847, 1982.
Woodstock and Taylorson, Plant Physiol., 67:424–428, 1981.
Crawford, New Phytologist, 79:511–517, 1977.
Johnson and Gagnon, New Forests, 2:65–72, 1988.
Nursten and Williams, Chem. Indust. 486–497, 1967.
Shamila et al., J. Food Sci. 57:1173, 1992.
Bressen et al., Plant Physiology 63:924–930, 1979.
Schjoerring, Trace Gas Emissions by Plants, 267–292, 1991.
Pratt and Goeschl, Ann. Rev., Plant Physiol. 20:541–584, 1969.
Freeman et al., Appl. Env. Microbiol., 32:222–231, 1976.
Beaudry et al., Plant Physiol., 85:277–282, 1987.
Liu, J. Amer.Soc. Hort. Sci., 101:63–65,1976.
Thompson and Seymour, Ann. Appl. Biol., 101:407–410, 1982.
Saltveit et al., J. Amer. Soc. Hort. Sci., 103:472–475, 1978.

* cited by examiner

*Primary Examiner*—Ralph Gitomer
(74) *Attorney, Agent, or Firm*—Ridout & Maybee

(57) ABSTRACT

A method of assessing the condition of a fruit, vegetable, plant, or flower is provided. The method includes maintaining the fruit etc. in a substantially gas tight enclosure to trap gases produced by the fruit etc. A sample of the trapped gases is removed and the concentration of at least one volatile gas in the sample is measured by contacting the sample with a colorimetric reagent that changes colour on contact with the volatile gas. The condition of the fruit etc. is assessed on the basis of the colour change of the colorimetric reagent.

17 Claims, 18 Drawing Sheets

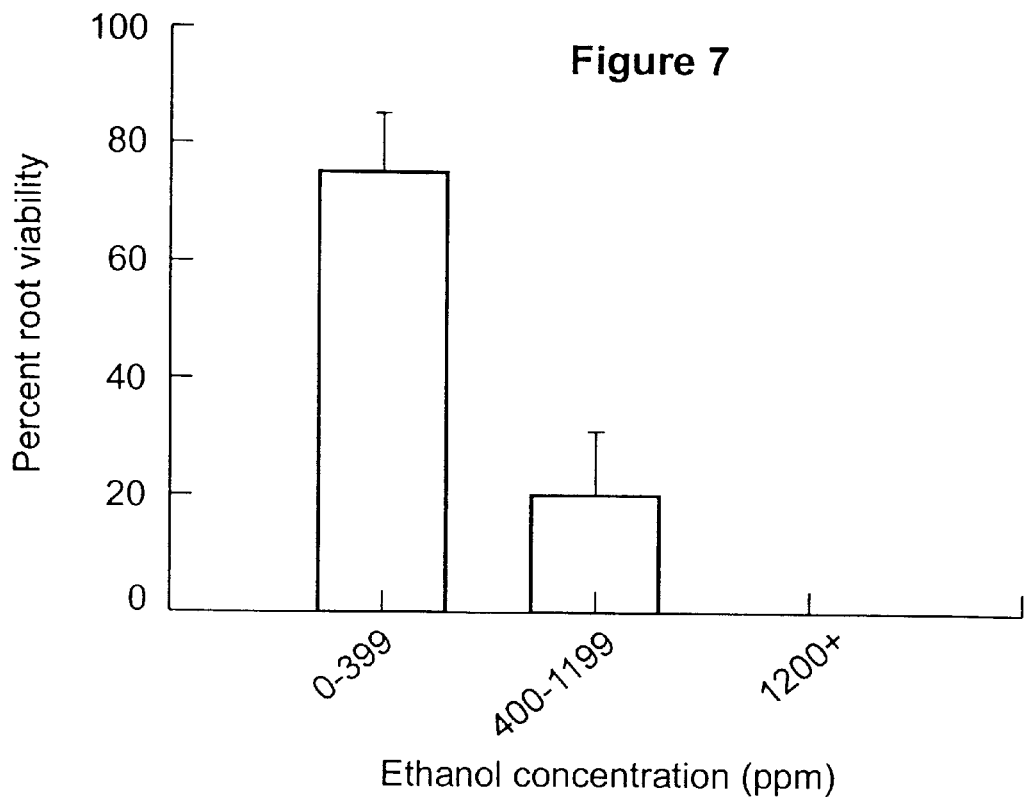
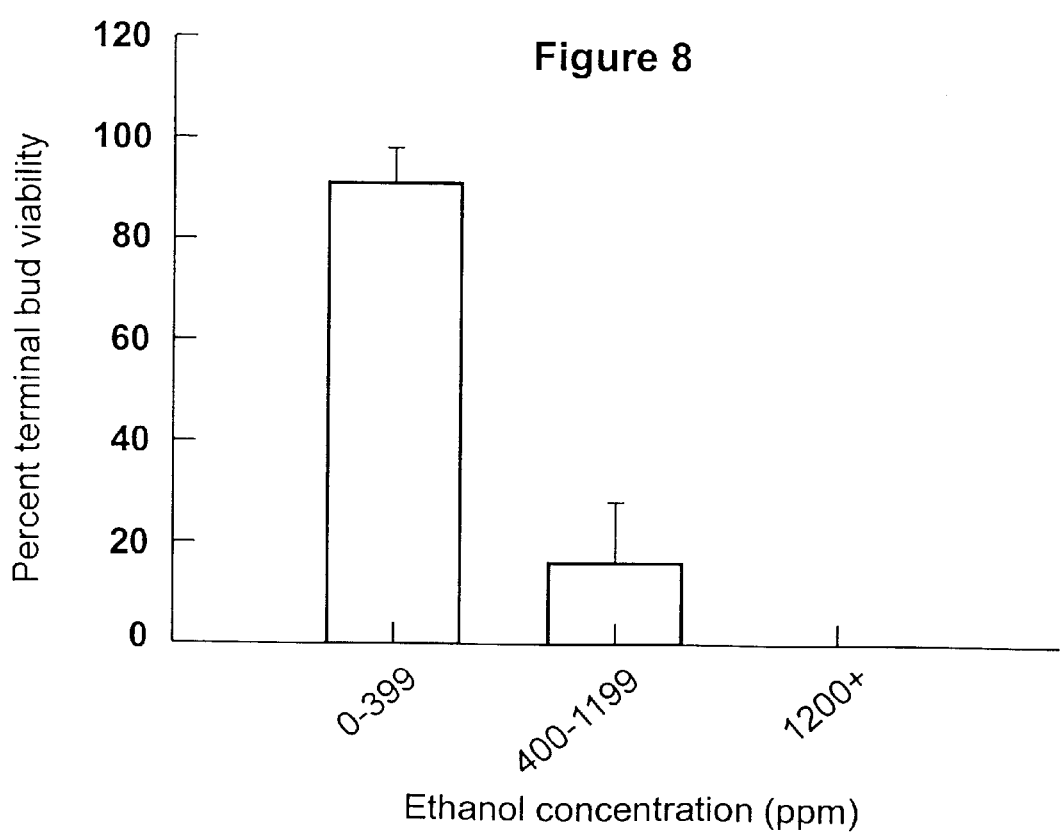

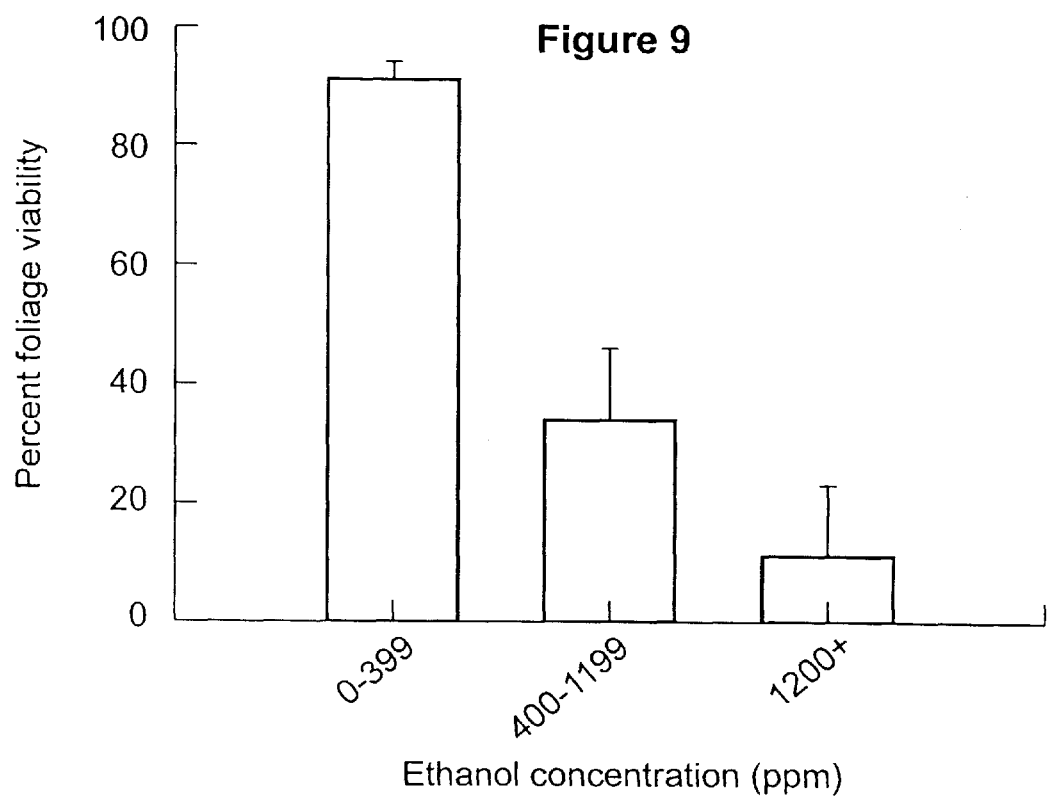
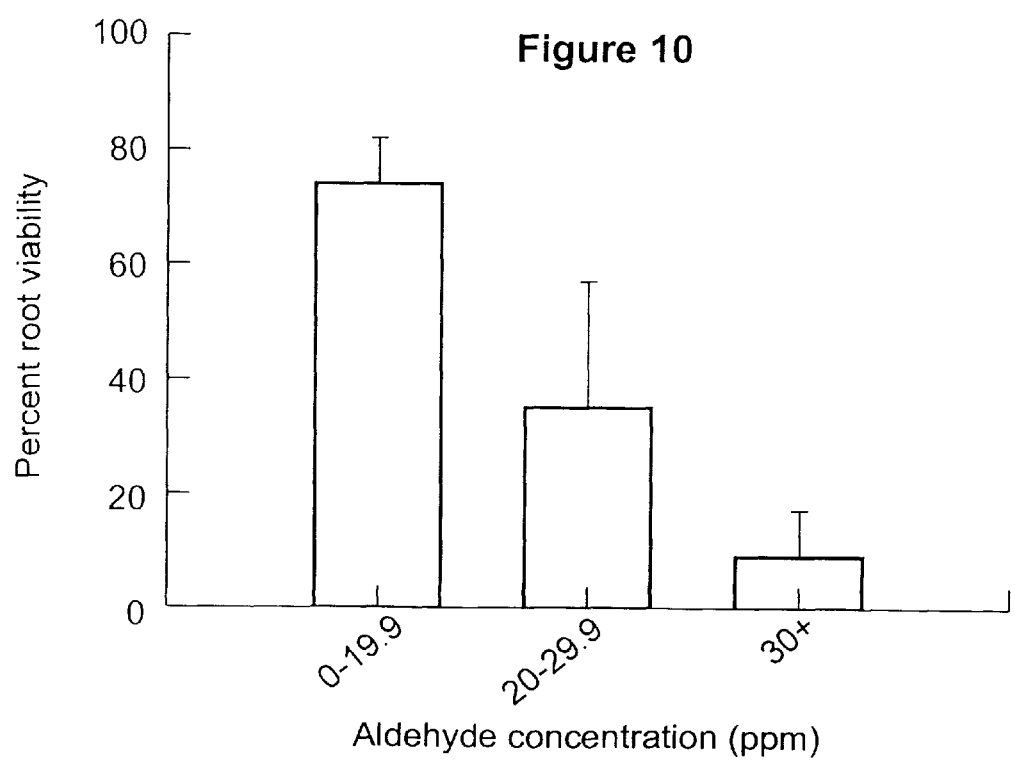

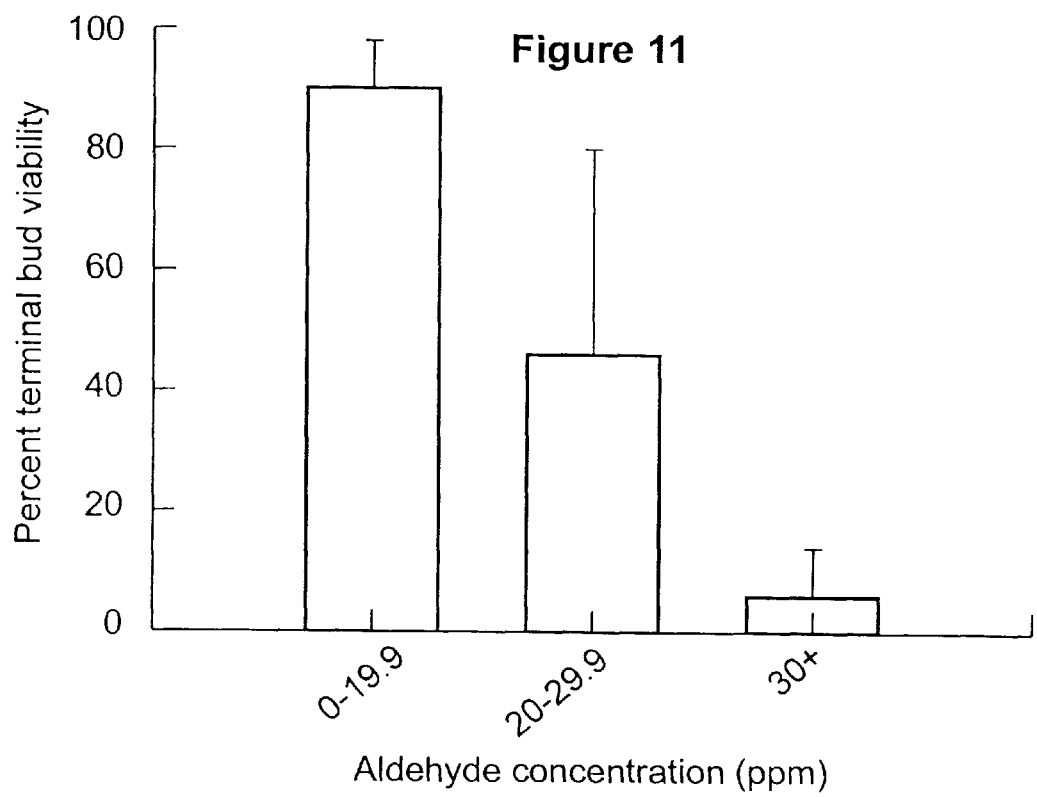
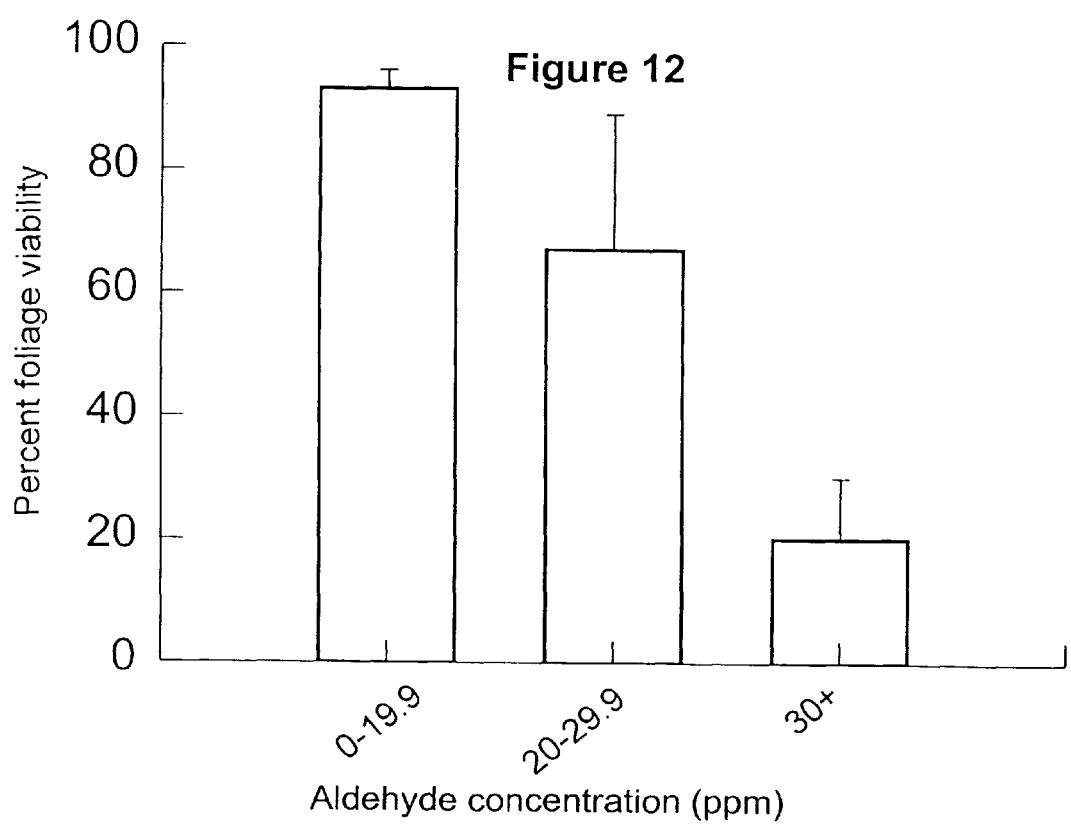

Ethanol values
(ppm read using 50 cc gas sample)

Acetaldehyde concentration (ppm)

METHOD FOR ASSESSING THE VIABILITY OF PLANT TISSUE USING A COLORIMETRIC REAGENT

This application is a continuation-in-part application of U.S. patent application Ser. No. 08/440,950, filed May 15, 1995, now abandoned.

FIELD OF THE INVENTION

This invention relates to assessing the viability of plant materials in general. In accordance with one aspect of the invention, a method and apparatus for assessing the viability of seedlings prior to planting is provided. In accordance with another aspect of the invention, a method and apparatus are provided for assessing the condition of fruits, vegetables, plants, and flowers.

BACKGROUND OF THE INVENTION

Plant materials are routinely assessed to determine their quality, viability or fitness for a particular purpose: Seeds, seedlings and propagating materials such as tubes, cuttings, bulbs and the like are assessed for their viability and growth potential prior to planting. Other agricultural products, such as fruits, grains, flowers and vegetables are also assessed for viability, freshness, consumability and storage life.

Assessment of viability or quality is particularly important when plant materials have been stored for extended periods or have been transported over long distances. Plant materials are subject to a wide range of stresses during storage and transport which can have serious affects on their subsequent viability and quality. Stresses to which plant materials may be subjected during storage and transport include cold temperatures, freezing, excessive heat, water deficit, physical stresses and chemical stresses from pollution. Although such stresses can seriously impact on the viability of plant materials and on their future potential for growth and storage, the affects may not be immediately apparent even from a close visual inspection of the materials.

The need for a method to assess viability of plant materials is particularly acute in the forestry industry where large scale seedling planting is an important aspect of reforestation and protection of renewable wood resources. Billions of tree seedlings and batches of seed are shipped annually for planting, frequently in remote areas. The recipients of the seeds and seedlings are frequently unaware of the stresses and damage to which the seeds and seedlings may have been subject, unless the damage is so severe as to be apparent from a visual inspection. Considerable expense and effort are involved in the planting and nurturing of young tree seedlings, which are frequently planted in large numbers over vast areas. Significant losses are incurred where stressed seedlings are planted which have poor viability and reduced growth potential, resulting in non-reforestation or low yield.

Typically the areas where replanting is to take place are in remote locations. Thus tree seedlings or plants to be planted must be transported to these locations from centrally located nurseries. Transportation may stress the trees, making them weaker and less viable or less suitable for planting. Because of the manual labour and expense involved in planting trees it is desirable to have as high a survival of planted trees as possible, namely that the tree seedlings be as fit as possible for replanting. In this manner seedlings have a maximum chance of surviving and growing vigorously. This helps in avoiding costly replanting.

One of the problems with tree seedlings is that it can be very difficult to evaluate plant viability in the field. To date visual inspections have been the main method of evaluation of plants immediately prior to planting. Such assessments though may not detect that the plant has been recently stressed in a way and to an extent which negatively impacts the seedlings' viability. In addition, such stress may not visibly manifest itself until many days or even weeks later.

The viability and quality of plant materials may be assessed by various laboratory analytical procedures to assess the affects of damage and stress. For example electrolyte leakage and chlorophyll fluorescence may be measured in the laboratory. The gases evolved by plants have been subjected to gas chromatographic analysis in the laboratory. Some trees have been shown to produce elevated levels of ethylene, ethene, acetaldehyde and ethanol in response to certain stresses (Kimmerer, T. W. and Kozlowski T. T. 1982. Plant Physiol. 69: 840–847).

Deterioration of seed has been shown to be accompanied by production of volatile gases, such as ethanol and acetaldehyde (Woodstock and Taylorson (1981) Plant Physiol. 67: 424–428; Crawford (1977) New Phytologist 79: 511–517). The viability of seeds is important as fields shown with poor quality seed may experience reduced yields at harvest due to lack of, or slow, germination. Furthermore, in agriculture, seeds of some plant species are consumed directly (e.g. rice) or are processed into food products (e.g. wheat and other grains for floor production).

Increased levels of acetaldehyde and ethanol in imbibing bean seeds subjected to accelerated aging treatments have been reported by Lowell, W. W. and Taylorson, R. B. (Plant Physiol. 1981, 67:424). Ethane levels in the head space gas from incubation tubes containing leaves or seedlings of loblolly pine have been measured by gas chromatography and correlated with electrolyte leakage as a possible method for assessing freeze damage (Johnson, J. D. and Gagnon, K. G. 1988, New Forests 2:65–72).

A wide variety of volatile emissions are also given off by several fruit species. (Nursten and Williams (1967) Chem. Indust. 486–497; and Mawele, S. M. et al, 1992, J. Food Sci. 57:1173). Fruits and vegetables produce many volatile compounds, for example, 37 compounds were identified by Nursten and Williams in pineapple (*Ananas sativus* L.). Some of these gases, such as ethanol, acetaldehyde and ethane, are related to stress and damage (Bressan et al. (1979) Plant Physiology 63: 924–930). However, the physiological significance of most of these compounds have not been elucidated.

There is no rapid and inexpensive method for field evaluation of volatile emissions produced by seedlings.

There is a need for a portable, inexpensive, non-destructive and reliable method for assessing viability and quality of plant materials outside the laboratory setting. In particular, foresters, nursery managers and farmers require a method for rapidly assessing damaged plants when damage occurs close to the time of shipping or planting. In forestry, screening for seedling viability is currently available at centralized facilities and takes at least 48 to 72 hours to obtain initial results and thus cannot provide the fast response required for on-site operational decisions.

BRIEF SUMMARY OF THE INVENTION

The invention generally relates to a simple, inexpensive and rapid method and apparatus for measuring concentrations of volatile gases evolved from plant materials and for directly correlating these measurements with viability of the plant material.

In accordance with one aspect of the invention, a method is provided for assessing viability of seedlings in the field by comparing colorimetric measurements of volatile gases evolved from the seedlings with measurements obtained from control seedlings.

The present inventors have surprisingly shown that spruce seedling viability is strongly correlated with the levels of gaseous ethanol and aldehydes evolved from the seedlings. The inventors surprisingly found a lower threshold amount of ethanol and aldehydes below which viability was not affected and an upper threshold amount above which seedlings were not viable. Thus the invention provides a method for identifying viable, damaged and non-viable seedlings prior to planting. For example, for black spruce seedlings, concentrations of ethanol below 1000 ppm where correlated with viable seedlings having little significant damage. Above this threshold measurement the seedlings were determined to be damaged and viability was affected and above levels of 2000 ppm seedlings were determined to be non-viable.

For white spruce seedlings, concentrations of ethanol below 300 ppm or concentrations of aldehyde below 20 ppm were correlated with viable seedlings having little significant damage. Above this threshold measurement the seedlings were likely to be damaged and at concentrations of ethanol greater than 1200 ppm or aldehyde concentrations greater than 30 ppm seedlings has very poor viability.

For loblolly pine (*Pinus taeda* L.) concentrations of ethanol below 10 ppm or concentrations of aldehyde below 250 ppm were correlated with viable seedlings having little significant damage. Above this threshold measurement the seedlings were likely to be damaged and at concentrations of ethanol greater than 750 ppm or aldehyde concentrations greater than 10 ppm seedlings had very poor viability.

The present invention thus provides a rapid and inexpensive method and apparatus for assessing the viability of plants and plant materials in the field based on the colorimetric measurement of volatile gases evolved by the plants or plant materials.

Therefore, the present invention contemplates a method of assessing the viability of a plant material, comprising the steps of; maintaining the plant material in isolation in a substantially gas tight enclosure to trap gases evolved from the plant material; removing a sample of the trapped gases; measuring a concentration of at least one volatile gas in the sample by contacting the sample with a colorimetric reagent that changes colour on contact with the volatile gas and; assessing the viability of the plant material on the basis of the colour change of the colorimetric reagent.

The plant material to be assessed may be, for example a seed, seedling, leaf, cutting, plant bulb, or tuber and the volatile gas may be ethanol or an aldehyde.

In a preferred aspect, the invention contemplates a method of assessing the viability of a seedling sample of a genus, species or cultivar of plant, comprising the steps of: maintaining the seedling sample in isolation in a substantially gas tight enclosure to trap gases evolved from the seedling sample; measuring a concentration of at least one volatile gas in the trapped gases by contacting the trapped gases with a colorimetric reagent that changes colour in contact with the volatile gas to be measured and; assessing the viability of the seedling by comparing the concentration of volatile gas to control concentrations of the volatile gas obtained from at least one control seedling sample of known viability.

A sample is assessed as non-viable when it has a concentration of volatile gas higher than a threshold concentration measured in the control seedling samples. The threshold concentration may be determined by exposing control seedling samples to different levels of stress to produce exposed seedling samples having quantitatively different levels of viability; quantitatively measuring the concentration at least one volatile gas evolved from the exposed seedlings as described above; and comparing the concentrations of volatile gas to the quantitative viability of the exposed seedlings to determine the threshold concentration of gas above which viability is affected or the threshold concentration of gas above which the exposed seedlings are non-viable.

The different levels of viability in the exposed seedlings may be quantitated based on one or more of the following factors: root growth, shoot growth, dormancy of terminal buds and foliage damage, the number of new roots, dormancy status of terminal bud, foliage damage, length of new terminal shoots, chlorophyll fluorescence and electrolyte leakage.

In a preferred embodiment, the plant is a tree. In a particularly preferred embodiment, the tree species is a white spruce or a black spruce.

The stress to which the control seedlings are exposed may be for example heat, cold, water deficit or pollution. The volatile gas may be ethanol or an aldehyde. In a preferred embodiment, the volatile gas is ethanol and the colorimetric reagent is potassium dichromate.

The invention further provides a portable apparatus for assessing the viability of a plant comprising: an air tight enclosure to house the plant being evaluated; a colorimetric indicator means for measuring a concentration of least one volatile gas inside of the enclosure, and a means for comparing the measured amount of the gas to an amount of the gas which has been correlated to one or more viability factors for the plant for determining the viability of the plant being evaluated.

In an embodiment, the apparatus further includes a pump for drawing a pre-determined volume of gas from the enclosure and a gas detection tube containing a colorimetric reagent which changes colour in response to certain concentrations of the volatile gas being measured. The apparatus may still further include a pump to create a flow of gas from inside of the enclosure out of the enclosure through the gas detection tube to measure the concentration of the volatile gas present in the enclosure.

In a still further embodiment, the gas detection tube includes calibration marks correlated to the amount of gas given off by plants which are viable and plants which are not viable.

In accordance with another aspect of the invention, a method is provided for assessing the condition of fruits, vegetables, plants, and flowers. The present inventors have found that the levels of ethanol and aldehydes evolved from fruits and vegetables correlates with the condition of the fruits, vegetables, plants, and flowers. In particular, the present invention have demonstrated that fruits, vegetables, plants, and flowers which have been subjected to a stress but do not have visible signs of damage can be identified based on the ethanol and aldehyde concentrations produced by the fruits, vegetables, plants, and flowers. In particular, the present inventors have demonstrated that bananas that have stress-induced damage and no visible damage, produce detectable levels of ethanol and aldehydes; in contrast to bananas that have no stress-induced damage which produce no detectable ethanol or aldehydes. Similarly, stress-induced non-visible damage to broccoli and cut flowers was detected based on production of ethanol and aldehyde gases.

The present invention have also demonstrated that the apparatus described herein is useful for evaluating the stage of ripening of a fruit or vegetable. The apparatus provides a simple, inexpensive and rapid means for measuring ethanol and aldehyde levels produced by fruits or vegetables thereby permitting evaluation of the stage of ripening.

Accordingly, broadly stated a method of assessing the condition of a fruit, vegetable, plant, or flower is provided comprising the steps of: maintaining the fruit, vegetable, plant, or flower in isolation in a substantially gas tight enclosure to trap gases produced by the fruit, vegetable, plant, or flower; removing a sample of the trapped gases; measuring a concentration of at least one volatile gas in the sample by contacting the sample with a colorimetric reagent that changes colour on contrast with the volatile gas and; assessing the condition of the fruit, vegetable, plant, or cut flower on the basis of the colour change of the colorimetric reagent. Preferably, the volatile gas which is assessed is one or both of ethanol and an aldehyde. Typically the fruit, vegetable, plant, or flower has no visible damage.

In an embodiment a method of assessing whether a fruit, vegetable, plant, or flower has stress-induced damage is provided comprising the steps of: maintaining the fruit, vegetable, plant, or flower in isolation in a substantially gas tight enclosure to trap gases produced by the fruit, vegetable, plant, plant, or flower; measuring a concentration of at least one volatile gas in the trapped gases by contacting the trapped gases with a colorimetric reagent that changes colour on contact with the volatile gas to be measured, preferably potassium dichromate, and; assessing the condition of the fruit, vegetable, plant, or flower by comparing the concentration of volatile gas to control concentrations of the volatile gas obtained from at least one control fruit, vegetable, plant, or cut flower having known stress-induced, or no stress-induced damage. Stress-induced damage refers to damage to fruits, vegetables, plants, or flowers resulting from exposure to heat, cold, and the various stresses associated with the production, shipping, and handling of the fruits, vegetables, and flowers. The method is typically used to assess stress-induced damage in fruits, vegetables, plants, or flowers which have no visible damage. The method is particularly useful in selecting fruits, vegetables, plants, and flowers which do not have stress-induced damage thereby facilitating storage and shipping of the products, and providing a longer shelf life for the products.

A fruit, vegetable, plant, or flower sample may be assessed as having stress-induced damage when it has a concentration of volatile gas higher than a threshold concentration measured in a control. The threshold concentration may be determined by exposing control fruit, vegetable, plant, or flower samples to different levels of stress to produce samples having different levels of damage, quantitatively measuring the concentration of at least one volatile gas preferably ethanol or an aldehyde, produced by the fruit, vegetable, plant, or flower, as described above; and comparing the concentrations of volatile gas to the damage observed for the exposed fruit, vegetable, plant, or flower, to determine the threshold concentration of gas above which the fruit, vegetable, plant, or cut flower has stress-induced damage.

The invention further provides a portable apparatus for assessing the condition of a fruit, vegetable, plant, or flower comprising: an air tight enclosure to house the fruit, vegetable, plant, or flower being evaluated; a colorimetric indicator means for measuring a concentration of least one volatile gas inside of the enclosure, and a means for comparing the measured amount of the gas to an amount of the gas which has been correlated to a degree of damage in the fruit, vegetable, plant, or flower. The apparatus may include a pump for drawing a pre-determined volume of gas from the enclosure, and a gas detection tube containing a colorimetric reagent which changes colour in response to certain concentrations of the volatile gas being measured. The apparatus may also include pump to create a flow of gas from inside of the enclosure out of the enclosure through the gas detection tube to measure the concentration of the volatile gas present in the enclosure. The gas detection tube may include calibration marks correlated to the amount of gas given off by a fruit, vegetable, plant, or flower which is damaged and those which are not damaged. The apparatus may be used to assess whether a fruit, vegetable, plant, or flower has stress-induced damage and it may be used to determine the stage of ripening of a fruit or vegetable.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Reference will now be made to the attached drawings, by way of reference only, which show preferred embodiments of the instant invention and in which:

FIG. 7 is a bar graph showing the relationship between ethanol concentration and percent root viability for white spruce seedlings;

FIG. 8 is a bar graph showing the relationship between ethanol concentration and percent terminal bud viability for white spruce seedlings;

FIG. 9 is a bar graph showing the relationship between ethanol concentration and percent foliage viability for white spruce seedlings;

FIG. 10 is a bar graph showing the relationship between concentration of aldehydes and percent terminal bud viability for white spruce seedlings;

FIG. 11 is a bar graph showing the relationship between concentration of aldehydes and the percentage terminal bud break for white spruce seedlings;

FIG. 12 is a bar graph showing the relationship between concentration of aldehydes and percent root viability for white spruce seedlings;

DETAILED DESCRIPTION OF PREFERRED EMBODIMENTS

Figure 1:
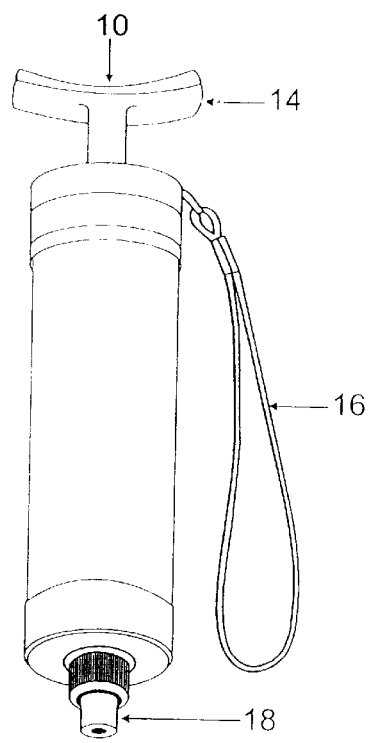
FIG. 1 shows a device for measuring volatile emissions from plants.

As previously noted the present invention is directed to a method and apparatus for assessing the viability of plant material. The term viability as used herein refers most broadly to the quality and health of the plant material and to its suitability for a particular purpose. Viable plant material is healthy and not damaged.

In accordance with one aspect, the present invention relates to a method of assessing the viability of a seedling sample, prior to the same being shipped or planted in the ground. The method includes a series of steps each of which are set out in more detail below.

In one aspect, the invention particularly relates to the assessment of viability of a seedling sample of a genus, species or cultivar of plant based on the colorimetric measurement of one or more volatile gases.

To assess viability using the methods of the invention a seedling sample is selected for evaluation. Any type of seedling may be selected, preferably tree seedlings, more preferably the seedling may be selected from the following species: white spruce *Picea glauca;* black spruce *Picea mariana;* white spruce *Pinus strobus;* red pine *Pinus resinosa;* jack pine *Pinus banksiana;* loblolly pine *Pinus taeda;* Norway spruce *Picea abies* and larch *larix* spp. Other suitable plant species include lettuce *Lactuca sativa*, broccoli *Brassica oleracea italica,* bananas *Musa sapientum,* peaches *Prunus serica* and Lactuca spp. It will be appreciated however that will reference is made to the foregoing and specific examples are provided herein with respect to certain of the foregoing, this invention is not restricted to these particular species as it is believed to be generally applicable to the seedlings of many other plant species and other types of plant material as described below.

Seedling samples may be particularly usefully assessed where there are reasons to be concerned about viability, for example after shipping or prolonged storage or where the seedlings may have been subjected to stresses such as excessive heat, cold, drought, pollution or disease. Assessment is useful prior to purchase, shipping or planting in order to select viable seedlings for these purposes.

For assessment, the seedling sample is maintained for a period in isolation in a substantially gas tight enclosure to trap gases evolved from the sample. Suitable enclosures include plastic bags or boxes. It is most preferred if the enclosure is completely air tight, but this may not always be possible in the field. However, the greater the leakage from the enclosure the less accurate the results become and so an essentially air tight enclosure is most preferred. It will be appreciated that the enclosure should provide suitable conditions for the maintenance of the plant material. The conditions selected will depend on the plant materials. For seedlings, appropriate temperature, light and humidity should be provided. The conditions selected will also depend on the volatile gas to be measured. For example, the temperature should be above the boiling point of the volatile gas to ensure that the gas is in the gaseous phase. The period of isolation and volume of the enclosure should be selected to permit comparison with gas measurements made in control seedling samples. The period of isolation need only be of sufficient duration to allow sufficient levels of volatile gas to accumulate in the enclosure. It is comtemplated that any period between 15 minutes and 7 days may be used, preferably between 1 and 24 hours, most preferably about 3 hours.

The concentration of the volatile gas or gases to be measured is measured by contacting the trapped gases from the enclosure with a colorimetric reagent that changes colour on contact with the volatile gas to be measured. Suitable colorimetric reagents may be selected based on the volatile gas to be measured. For example potassium dichromate, hydroxylamine and palladium sulphate may be used for measuring ethanol, aldehydes and ethylene respectively.

In a preferred embodiment, the colorimetric reagent is contained in a gas detection tube, through which the gases may be passed. Gas detection tubes are known in the art and generally consist of sealed elongate cylindrical enclosures of transparent material such as glass, pyrex or clear plastic. Preferably, the gas detection tube is used in combination with a pump for drawing a predetermined volume of the entrapped gases out of the enclosure and through the tube. The distance along the tube over which a colour change occurs in relation to the length of the tube provides a visual measure of the amount of the volatile gas in the entrapped gases. Suitable systems incorporating gas detection tubes and pumps are described for example in U.S. Pat. No. 3,388,975 and also include the portable gas analysis system manufactured by Gastec® Corporation, Tokyo, Japan). In a particularly preferred embodiment the gas detection tube has calibration marks correlated to the threshold amount of a volatile gas evolved by plants which are viable, plants which are viable but damaged and plants which are not viable.

Figure 3:
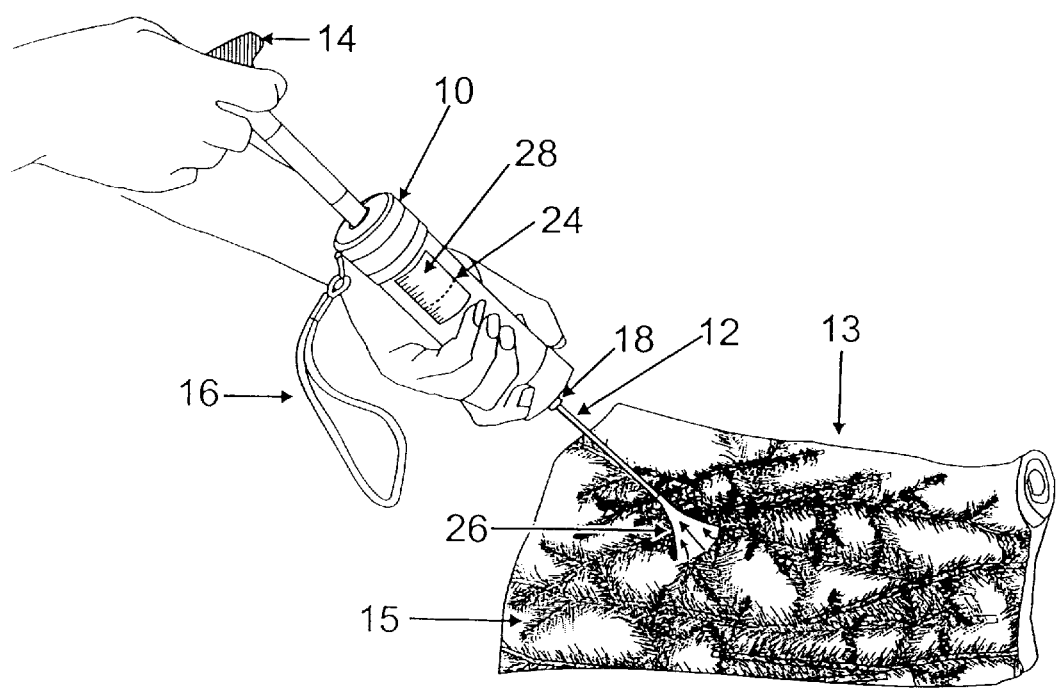
FIG. 3 is a view of a gas sample being taken with the device of FIG. 1.

In a preferred embodiment, the gas analysis system comprises a pump such as shown as 10 in FIG. 1, and gas detection tubes shown as 12. The pump is relatively small and preferably small enough to be easily transportable, such as in the glove compartment of a car or truck. The pump 10 includes a pull handle 14 and a carrying strap 16. At an end of the pump 10 remote from the handle 14 is a connector 18. One gas detection tube 12 at a time can be placed in connector 18. The gas detection tube 12 is then inserted into an enclosure 13 containing seedlings 15. Thus when the pull handle 14 is drawn out pulling out piston 24, air is drawn through the gas detection tube and into the body of the pump 10 (shown in FIG. 3 as arrows 26). Preferably the pump is provided with markings 28 to permit a specific amount of gas to be drawn through the gas detection tube and into the body of the pump 10. It is most preferred if the pump is capable of drawing predetermined fixed volumes of air through the tube, such as for example, 50, 100 or 200 cc of gas, so a concentration of gas can be measured. The pump made by the Gastec Corporation of Tokyo, Japan has been found suitable. Other suitable pumps include those employed in mine safety appliances, for example those manufactured by Drager or MSA.

Figure 2:
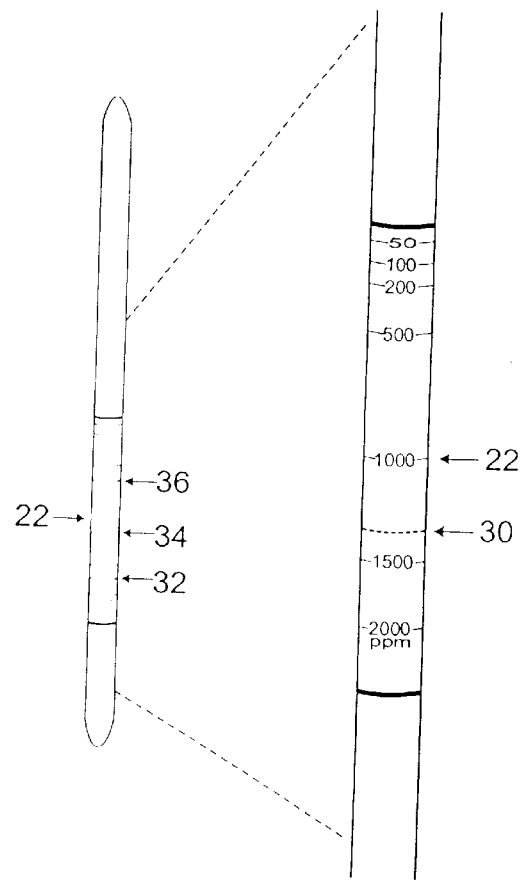
FIG. 2 is an enlarged view of a pair of gas detection tubes as shown in FIG. 1.

The gas detection tubes 12 are shown in more detail in FIG. 2. They are most preferably generally disposable and contain colorimetric reagents. The tubes come sealed at both ends and when a reading is required all that is necessary is to break off the ends and expose the tube to the air being tested. A change in colour is thus indicative of a certain concentration of a particular reactant (i.e. volatile gas) to which the tube is exposed. The exterior of the tube is graduated at 22 to indicate the number of parts per million of the target volatile gas in the air sample. The leading edge of the colour change indicates the concentration. The tubes 12 are then visually assessed for the gas concentration, and the viability of the plant material evaluated in accordance with the protocol below.

Suitable results have been obtained by using gas detection tubes available from Gastec, but there are also other suppliers of these types of pumps and gas detection tubes. It will be noted that the most preferred form of the tube is one which has been calibrated to have gradations on it specific to the application of this invention. In some cases it may be desirable to provide a single mark, which would be a pass fail mark shown schematically as 30 in FIG. 2. In other words, gas concentrations above the mark would mean that the plant or tree seedling being tested was not likely viable and should not be planted. In other cases it may be preferred to provide a plurality of marks which indicate likely viability (and hence vigour) shown schematically as 32, 34 and 36. While the gas reaction tubes are commercially available which indicate ppm concentrations in absolute terms, it is most preferred to custom calibrate such in accordance with this invention to make them genus, species or cultivar specific. As will be explained in more detail below, the exact position of the marks will depend upon the isolation protocol used and the specific genus, species or cultivar and gas being considered.

Further, it will be appreciated by those skilled in the art that while reference is made in the preferred embodiment to gas detection tubes other types of colorimetric systems for measuring gas concentration may also be suitable. In cases where the enclosure is of fixed and known dimensions, the gas concentration indicator could take the form of a sealed card or the like which is exposed to the air in the enclosure. Thus reference is made herein to a means for measuring gas concentration, which preferably includes a visual colour indication of gas concentration.

It will now be appreciated that the foregoing description relates to measuring the concentration of the volatile gases within the enclosure. Measuring concentration is possible because the pump permits a specific volume of gas to be withdrawn from the enclosure, to provide a concentration measurement. It will be appreciated that the enclosure could be modified to contain a set volume, and the measurement could be of the total or some defined portion of the total volume, and in this manner concentration measured. However, since it can be difficult in the field to establish good control over the volume in the actual enclosures (especially if they are merely plastic bags which are readily available, cheap and efficient) the most preferred method is to remove a fixed volume from the enclosure and to determine concentration based on this known volume.

As noted above, the viability of the seedling is assessed by comparing the concentration of volatile gas to concentrations of the volatile gas obtained from a control seedling sample of known viability. It will be appreciated that healthy (viable) controls seedlings may be used as a basis of comparison and significant differences from such control measurements may be taken as indicative of reduced viability.

Preferably, to obtain more detailed information about viability of the seedling sample, measurements are taken from a range of control seedlings which have quantitatively different levels of viability. For example control seedling samples may be exposed to different levels of stress to produce seedlings having quantitatively different levels of viability. The levels of the volatile gas evolved by these control seedlings can then be measured as described herein and the levels can be correlated to the viability of the control seedlings.

The control seedlings may be subjected to any suitable stress, such as heat, cold, water deficit, physical stress, such as shaking, chemical stress, such as pollution. The manner in which the stress is applied is not believed to be too critical, however the most preferred form of stress is that type of stress the seedling is likely to be subjected to prior to it being used, so as to emulate the same. Thus for tree seedlings which have to be transported over large distances by train or truck, and stored on site for a period of time prior to planting, the preferred type of stress is thought to be exposed to elevated temperatures for periods of time of up to several days, such as might occur prior to planting tree seedlings. One preferred manner of stressing is set out in more detail below in the examples.

The control seedlings that have been stressed are planted under controlled growing conditions and allowed to develop naturally. Then after a predetermined elapsed growing time, the materials are quantitatively evaluated for viability and growth. There are a variety of growth factors that can be measured, but the most preferred ones include, root, bud and foliage viability tests including measuring the length and number of any new roots produced; measuring the percent of needles that are healthy and measuring the buds that have broken open, signifying growth. It will be appreciated by those skilled in the art that other parameters might also be measured, provided that the same are related to the general viability of the plant being considered and that while reference is primarily made to these growth factors, this invention is not limited to these specific growth factors but is intended to comprehend any growth or physiological performance factors (quality factors) which can provide a measure of the damage suffered by the plants.

The viability of the control seedlings may be measured using techniques known to those skilled in the art, such as visual and microscopic inspection, chlorophyll fluorescence, electrolyte leakage, status of roots, shoots, foliage, buds, observing growth and survival.

In a preferred embodiment, the seedling is a tree seedling and the viability is determined by measurements of at least one of the following: electrolyte leakage; chlorophyll fluorescence; growth performance including number of new roots, terminal bud viability and foliar damage.

The volatile gases to be measured may include a wide range of volatile gases, which are known to be evolved from plant materials (Nurnsten and Williams, 1967, supra). Suitable gases include hydrocarbons, alcohols, acids, carbonyls, hydroxy compounds, and esters. Preferably, the following volatile gases are measured: ethanol, aldehydes, ethane, ethylene. Most preferably the volatile gases are ethanol and aldehydes. It will be appreciated that the term aldehyde refers to a broad class of compounds having the general formula RCHO, and characterized by an unsaturated carbonyl group (C=O). Colorimetric reagents may be selected which damage colour in response to a wide range of aldehydes or in response to specific aldehydes, such as acetaldehyde or formaldehyde.

Volatile gases such as terpenes may be produced by plants in response to insects and fungal pathogens, and their levels in the air in a plant community or ecosystem may indicate viability of the plants in the ecosystem. Isoprene (C5H8) production, another common volatile emission from plants, may be indicative of photosynthesis (Sanadze (1991) In: "Trace Gas Emissions by Plants", Academic Press). High rates of isoprene emission by plants may reflect high rates of photosynthesis, an indication of high plant growth rates, yield and viability.

Once the data has been collected, the plant viability measurements are correlated to the amounts of volatile gas measured. One convenient way of correlating the results is to plot on a graph measured volatile gas concentration vs plant growth (viability) parameter. Statistical evaluations can then be made to determine the best fit or best correlation and to include a margin of error. The statistical analysis of the results will be understood by those skilled in the art, and are discussed in more detail with reference to the specific examples.

The relationship between the viability of the plant material and the concentration of the volatile gases evolved may be determined by regression analysis as described in the examples herein. An analysis of variance may be used to assist in the determination of the location of thresholds corresponding to viable, damaged and non-viable plant materials. Accordingly, the present method provides a simple method for identifying and selecting viable, damaged and non-viable plant material.

The present method permits the identification of the threshold amounts of volatile gas above which seedlings are damaged, as indicated by significant reductions in one or more of the viability factors quantitated. Seedlings under assessment producing levels of the gas under this threshold amount may be considered to be fully viable. Seedlings producing levels of gas over this threshold may be classed as damaged. The method also permits the identification of the threshold amounts of volatile gas above which seedlings will not survive and grow and seedlings under assessment producing levels of gas over this threshold may be classed as being non-viable.

The present method also permits a determination of specific viability parameters. For example, where the correlation between a specific viability parameter and the concentration of volatile gas evolved has been established, than a volatile gas measurement from a test seedling may be used to determine whether the seedling will be viable for the specific parameter. Thus root, shoot, bud or foliage viability may be individually determined based on the measured concentration of volatile gas evolved by the test seedling.

It is an advantage of the methods and apparatus of the present invention that they are inexpensive. Gas detection tubes are not costly and are readily available. It is a particular advantage that the method may be carried out in remote locations as the apparatus is light and portable and can easily be carried into remote locations for rapid testing in the field by persons not having any specialized laboratory or scientific skills. It is a further advantage that the method is non-destructive and plants which have been tested may be planted or used for their intended purpose after the test is complete.

One aspect of the present invention must be understood is that in certain circumstances it is possible to obtain false positive readings using the foregoing techniques. This would occur for example where the plants being evaluated were so severely damaged that the ethanol producing systems, for example, were no longer functional; substantially dead tissues do not exhibit this behaviour of producing certain volatile gases. Thus a visual assessment of the plant material to be evaluated initially is preferred to prevent such false positive readings from being relied upon. In other words, specimens with severe symptoms of damage (like dead foliage or visible disease) should be evaluated with caution. However this is relatively easy to do since at the point at which volatile gas production drops off, visible necrosis of foliage or other damage symptoms are usually apparent.

As noted above, it is contemplated that a wide range of plant materials may be assessed by the methods and apparatus of the invention such as seeds, seedlings, plants, bulbs, tubers, parts of plants such as cuttings and leafs, and propagating materials. Of course as will be understood from the description below there must be enough of the plant or plant material being tested to provide a representative and repeatable result, but provided that this requirement is met, the method is believed applicable.

In a preferred embodiment, the methods and apparatus of the invention may be used to assess the viability of plant materials to be planted, grown or propagated. In a particularly preferred embodiment, the methods and apparatus are useful for assessing the viability of seedlings, most preferably tree seedlings. The method can be applied in the field to identify tree seedlings that are not viable and which would not survive planting or which have poor growth potential. These seedlings can then be rejected, saving the effort and expense of planting, nurturing and then having to replant. Viable seedlings, suitable for planting and having strong growth potential may also be identified. In a broader sense, viability may include a measure of suitability for replanting.

The methods and apparatus of the invention may also be useful for assessing the viability of seeds prior to planting or prior to consumption. It will be appreciated that assessment of viability may play a role in assessing a general ecosystem condition as the biogenic synthesis of gases (i.e. gases produced by biological processes) can indicate the status or condition of plant communities and ecosystems. For example, ammonia volatilized from plants can indicate the nitrogen status of plants and the presence of fungal diseases (Schjoerring (1991) In: "Trace Gas Emissions by Plants", Academic Press).

A method and apparatus are described herein for assessing the condition of fruits and vegetables. Levels of gases evolved from the fruits or vegetables have been found to be correlated to the condition of the fruits and vegetables. Any fruits and vegetables that produce gases that correlate with the condition of the fruits and vegetables may be assessed using the method and apparatus described herein. The use of the method and apparatus of the invention has been illustrated in the examples for bananas and broccoli.

The methods and apparatus also have application to the horticulture and floriculture industries for the assessment of the condition of a wide variety of ornamental plant species and cultivars, and flowers from the plants. During the production, shipping and handling of plants, plant tissues, or flowers, or any horticultural or floricultural species, stressful conditions may reduce plant quality and viability. It has been demonstrated that the measurement of gases such as ethanol and aldehyde produced by cut flowers having no visible damage is useful in selecting flowers which have not been exposed to substantial stress. Therefore, the gas measurements may be useful in predicting the shelf life of cut flowers. Measurement of gases such as ethylene may also be used in regulating flower production. The methods and apparatus described herein may be used to assess the condition of annual plants (e.g. Chrysanthemum, Dianthus carnation), herbaceous perennial (eg. Begonia, Lilium (lily)), and woody plants (eg. Rosa (rose), Syringa vulgaris (lilac)), and flowers from these plants.

"Condition" of a fruit, vegetable plant, or flower refers to one or more of its freshness, ripeness, palatability, readiness for harvest (e.g. abscission of fruit from plants, color), nutritional quality (e.g. changes in carbohydrate composition, protein content, organic acid composition, development of wax on the skin and changes in pectin composition leading to fruit or vegetable softening, aromas imparting fruit flavor), and suitability for consumption. Measurement of the gas concentrations produced by fruits, vegetables, and flowers may be used to obtain an objective measure of the condition of the fruits, vegetables, and flowers thus permitting the selection of fruits, vegetables, and flowers which are particularly suitable for shipping and storage, and which will have a longer shelf life.

The measurement of gases produced by fruits, vegetables, plants, and flowers (eg. ethanol and aldehyde) may be used to determine if fruits, vegetables, plant or flowers have stress-induced damage. Stress-induced damage refers to damage to fruits, vegetables, plants or flowers resulting from exposure to heat, cold, physical stress, chemical stress, and the various stresses associated with the production shipping, and handling of the fruits, vegetables, plants, and flowers. Typically the methods described herein are used to assess stress-induced damage in fruits, vegetables, plants, or flowers which have no visible damage.

During ripening, fruits and vegetables of virtually all species produce gases, one of the best known being ethylene ($C_2H_4$). Levels of production of gases such as ethylene by fruits and vegetables are associated with readiness for harvesting, and their palatability and nutritional quality (e.g. changes in carbohydrate composition, protein content, organic add composition, development of wax on the skin and changes in pectin composition leading to fruit or vegetable softening, aromas imparting fruit flavor) (Pratt and Goeschl (1969) Ann. Rev. Plant Physiol. 20: 541–584; Nursten and Williams (1967) supra). The apparatus described herein is useful for evaluating the stage of ripening of a fruit or vegetable. The apparatus provides a simple, inexpensive and rapid means for measuring ethanol and aldehyde levels produced by fruits or vegetables hereby permitting evaluation of the stage of ripening.

In an embodiment, a method of assessing the condition of a fruit, vegetable, plant, or flower is provided comprising the steps of: maintaining the fruit, vegetable, or cut flower in isolation in a substantially gas tight enclosure to trap gases evolved from the fruit, vegetable, or cut flower; removing a sample of the trapped gases; measuring a concentration of at least one volatile gas in the sample by contacting the sample with a colorimetric reagent that changes colour on contact with the volatile gas and; assessing the condition of the fruit, vegetable, or cut flower on the basis of the colour change of the colorimetric reagent. In a preferred embodiment, the method is used to assess whether a fruit, vegetable, or cut flower has stress-induced damage.

Suitable gas tight enclosures for use in the method have been described herein and include plastic bags or boxes. Preferably the enclosure is completely air tight, since the greater the leakage from the enclosure the less accurate the results become. When the method is used to assess plants, the enclosure should provide suitable conditions for the maintenance of the plants. The conditions selected will depend on the type of plant. The conditions selected will also be selected depending on the volatile gas to be measured. For example, the temperature should be above the boiling point of the volatile gas to ensure that the gas is in the gaseous phase. The period of isolation and volume of the enclosure should be selected to permit comparison with gas measurements made in control samples. The period of isolation need only be of sufficient duration to allow sufficient levels of volatile gas to accumulate in the enclosure. It is contemplated that any period between 15 minutes and 7 days may be used, preferably between 1 and 24 hours, most preferably about 3 hours.

The concentration of the volatile gas or gases is measured by contacting the trapped gases in the enclosure with a colorimetric reagent that changes colour on contact with the volatile gas to be measured. Suitable colorimetric reagents are selected based on the volatile gas to be measured. Potassium dichromate, hydroxylamine and palladium sulphate may be used for measuring ethanol, aldehydes and ethylene, respectively.

In a preferred embodiment, the colorimetric reagent is contained in a conventional gas detection tube as described herein, through which the gases may be passed. The gas detection tube is typically used in combination with a pump for drawing a predetermined volume of the entrapped gases out of the enclosure and through the tube. Suitable systems incorporating gas detection tubes and pumps are described herein and include the systems described in U.S. Pat. No. 3,388,975 and the portable gas analysis system manufactured by Gastec® Corporation, Tokyo, Japan). The gas detection tube may have calibration marks correlated to the threshold amount of a volatile gas produced by fruits, vegetables, plants, or flowers which are damaged, ripened etc. In a particularly preferred embodiment, the gas analysis system comprises a pump such as shown as 10 in FIG. 1, and gas detection tubes shown as 12 and in FIG. 2, and as particularly descried herein.

Other types of colorimetric systems for measuring gas concentration may also be employed to assess fruits, vegetables, plants, and flowers. In cases where the enclosure is of fixed and known dimensions, the gas concentration indicator could take the form of a sealed card or the like which is exposed to the air in the enclosure.

The apparatus i.e. gas detection system described herein permits a specific volume of gas to be withdrawn from the enclosure, to provide a concentration measurement. As discussed herein, the enclosure could be modified to contain a set volume, and the measurement could be of the total or some defined portion of the total volume. Preferably, a fixed volume is removed from the enclosure and gas concentrations are based on this known volume.

The condition of the fruits, vegetables, plants, or flowers is assessed by comparing the concentration of volatile gas to concentrations of the volatile gas obtained from controls having a known condition. Measurements may be taken from a range of control fruits, vegetables, plants, or cut flowers which have different conditions. For example, control fruit, vegetable, plant, or flower samples may be exposed to different levels of stress to produce fruits, vegetables, plants, or flowers having different conditions. The levels of the volatile gas produced by these controls can then be measured as described herein and the levels can be correlated to the condition of the fruits, vegetables, plants, or flowers.

The control fruits, vegetables plants, or flowers may be subjected to stresses, such as heat, cold, water deficit, physical stress, chemical stress, such as pollution, and the various stresses associated with the production shipping, and handling of the fruits, vegetables, plants, and flowers. The condition of the controls will be determined by observing the fruits, vegetables, or flowers. For example, for bananas, the extent and time of bruising may be determined after exposure to the stress; and, for flowers changes in color or flower drooping may be assessed after exposure to the stress.

The volatile gases to be measured may include a wide range of volatile gases, which are known to be produced by fruits, vegetables, plants and flowers. For example, the volatile gases which may be measured include hydrocarbons, alcohols, acids, carbonyls, hydroxy compounds, and esters. Preferably, the following volatile gases are measured: ethanol, aldehydes, ethane, ethylene. Most preferably, the volatile gases are ethanol and aldehydes (see definition herein).

The observed condition of the control fruits, vegetables, plants or flowers (i.e. damaged v. undamaged, ripened vs. unripened etc.) is correlated to the amounts of volatile gas measured. The condition of the plant versus the volatile gas concentration may be plotted on a graph and statistical evaluations can be made to determine the best fit or best correlation and to include a margin of error. The relationship between the condition of the material and the concentration of the volatile gases may be determined by regression analysis as described more particularly herein.

The present method permits the identification of the threshold amounts of volatile gas above which fruits, vegetables, plants, and flowers have stress-induced damage or will have an undesirable characteristic. Fruits, vegetables, plants, and flowers producing levels of gas under the threshold amounts represent fruits, vegetables, plants, and flowers with desirable conditions, e.g. no stress-induced damage. Fruits, vegetables, plants, and flowers producing levels of gas over this threshold may be classed as damaged, or undesirable.

Other possible applications for the methods and apparatus described herein include assessing viability, shelf life and suitability for consumption of dairy and meat products as a wide variety of volatile chemicals are associated with the spoilage of diary and meat products. (Freeman et al. (1976) Appl. Env. Microbiol. 32(2): 222–231).

The following non-limiting examples are illustrative of the present invention:

EXAMPLES

Example 1

Analysis of Stress-Induced Black Spruce Seedling Damage

Plant Material

Black spruce tree seedlings from Ontario site region 32-34-000 were obtained from an operationally produced bare-root crop grown at the Swastika Tree Nursery (48°02'N., 80°22'W.). Trees were operationally lifted between Oct. 23 and 28, 1992, and stored frozen at $-2°$ C. prior to being received.

Seedling Handling

In April 1993, 4 polyethylene-lined paper bags, each containing between 200 and 250 seedlings were transported to the Ontario Forest Research Institute in Sault Ste. Marie, Ontario. The seedlings were maintained in frozen storage at $-2°$ C. then thawed in the bags at $2°$ C. for 10 days immediately prior to heat treatment. The experiments were repeated once on June 16, June 21 and twice on July 7. Each replication consisted of one bag of seedlings allowed to heat in a greenhouse. After thawing, a bag of seedlings was taken to the laboratory and allowed to warm to room temperature (approximately $20°$ C.) overnight. After internal bag temperature reached $20°$ C., two or three ethanol gas measurements per bag were made using a portable gas analysis system (control value). The portable gas analysis system was manufactured by Gastec® Corporation, Tokyo, Japan). The bag containing the remaining seedlings was resealed and placed in a greenhouse for stress treatment. This procedure was repeated separately for each of the four bags of seedlings.

Stress Treatments

Heat treatments were used to simulate potential operational conditions in the field, where bags of seedling may be exposed to direct sunlight and warm temperatures for several days prior to planting. A range of levels of seedling stress was created by heating seedlings in their bags in a greenhouse at ambient temperatures. The maximum temperature in the greenhouse during the exposure period was $36°$ C. Durations of heating were arbitrarily chosen to provide a range of stress levels and differed each time the experiment was repeated depending upon the intensity of the light and ambient temperature. Exposure periods ranged from 3 hours to 7 days. After each exposure period, the bag of seedlings was returned to the laboratory and allowed to cool to room temperature. When internal bag temperature reached $20°$ C., two or three ethanol gas measurements per bag were made. An average ethanol concentration was calculated for each exposure period. After measurement of ethanol gas concentration, 20 seedlings were removed from the bag and potted for performance analysis. The bag was then resealed and returned to the greenhouse for further heat treatment. From three to seven exposure durations were used to obtain a range of seedling stress levels and gas concentrations.

Stress-Induced Ethanol Gas Analysis

A portable gas analysis system, composed of a gas vacuum pump and gas detection tubes were used to determine the concentration of ethanol produced by differentially stressed seedlings. The gas is drawn by vacuum through a disposable gas detection tube attached to the end of a vacuum pump. The gas detection tube is packed with orange potassium dichromate. If gaseous ethanol is present in the air passing through the tube, it reacts with the potassium dichromate to produce light-blue chromic sulphate. The exterior of the tube is graduated to indicate the number of parts per million of ethanol gas in the air sample. The leading edge of the colour change indicates the concentration of ethanol in the sample.

Gas samples were collected as follows. The internal temperature of a bag of seedlings was brought to $20°$ C.$\pm 1°$ C. by incubation in the laboratory. A gas detection tube was attached to the vacuum pump and inserted approximately 6 cm through a 1 mm diameter hole in the bag containing the seedlings.

The vacuum pump was manually operated to withdraw 100 cm$^3$ of the gases from the bag through the gas detection tube. After approximately three minutes sampling was complete and the tube was removed from the bag of seedlings. Gas concentration was estimated after a further five minutes by observing the position of the colour change in the gas detection tube.

Black spruce seedlings were handled and stressed generally as described above. Twenty seedlings for each control and stressed group of seedlings removed from the bags immediately following gas extraction. Two seedlings per pot were planted in 3-L pots, using a 2:1 (v/v) peat; vermiculite substrate, watered and placed into a controlled environment (26° C.:18° C. day:night temperature); 70% relative humidity; 250 μmol. m-2 s$^{-1}$ photosynthetic photon flux density, PPFD) to allow the damage symptoms to develop and for growth to occur.

After 14 days the seedlings were examined to determine the number of new roots, dormancy status of the terminal bud, foliage damage and length of new terminal shoots. Seedlings were removed from their pots, and the number of white root tips over 1 cm long were counted (root growth potential). The main stem terminal bud of each tree was evaluated to determine bud break. If a terminal bud failed to break it was bisected longitudinally and examined for tissue browning. Each seedling was evaluated visually to classify needle damage and undamaged needles in 10% classes.

The terminal 2 cm of the shoots of 10 randomly selected seedlings for each treatment were removed and placed in test tubes containing 30 ml distilled water. The shoot tips were incubated for 20–24 hours at 20° C., then the electrical conductivity (EC initial) of the solution was measured using a conductivity meter. Shoot tips were killed in a 90° C. oven for 3 hours, re-incubated for 20–24 hours at 20° C. and the electrical conductivity (EC killed) was re-measured. The percent relative conductivity was calculated as the initial conductivity×100/killed conductivity. Relative conductivity was used as an indicator of cellular membrane damage (Colombo et al. 1994).

Chlorophyll fluorescence total yield (Genty et al 1988), Schreiber and Nilger 1993) was measured on 10 potted seedlings (one seedling per pot), after 48 hours of growth in the environmental chamber. Needles near the top, middle and bottom of the seedling were measured using a PAM 2000 fluorometer (Heinz Waltz GmbH, Effeltrich, Germany). The three measurements were averaged to estimate fluorescence yield for each plant.

Data from four trials were combined for regression analysis. Best-fit nonlinear regressions with 95% confidence intervals were used to describe the relationships between ethanol concentration and the number of new roots, bud dormancy status, and foliar damage. Linear regressions were performed using the computer programs Sigmaplot© and SigmaStat© (Jandel Scientific, San Rafael, Calif. U.S.A.).

Analysis of variance (ANOVA) was used to assist in the determination of the location of thresholds corresponding to undamaged, damaged and severely damaged categories. A separate ANOVA was calculated for each of the four trials. In the ANOVA model bags of seedlings exposed to elevated temperatures for different durations (labelled by ethanol concentration) were used as treatments. A replication was defined as a pot containing two seedlings. The ANOVA models were slightly different (because of differing numbers of treatments) for each experiment. Values of foliar damage were modified by an arcsine transformation prior to ANOVA analysis. Percent bud break of seedlings from bags with different ethanol levels was compared using $X^2$ analysis.

Figure 4:
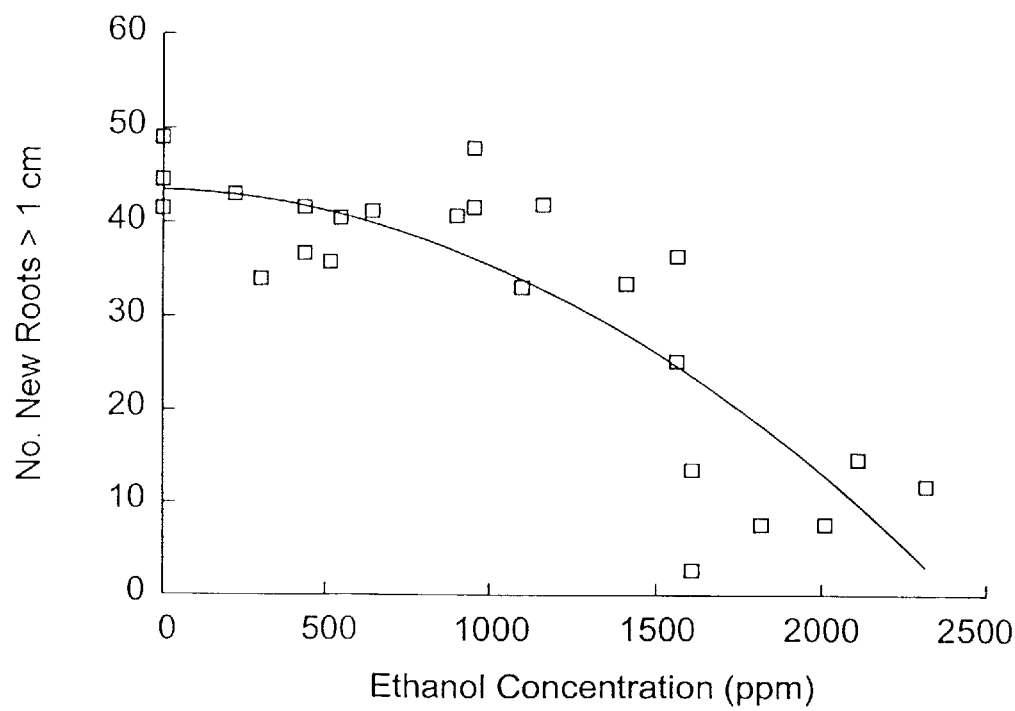
FIG. 4 is graph showing the relationship between ethanol concentration and the number of new roots produced which are over 1 cm long for black spruce seedlings.
Figure 5:
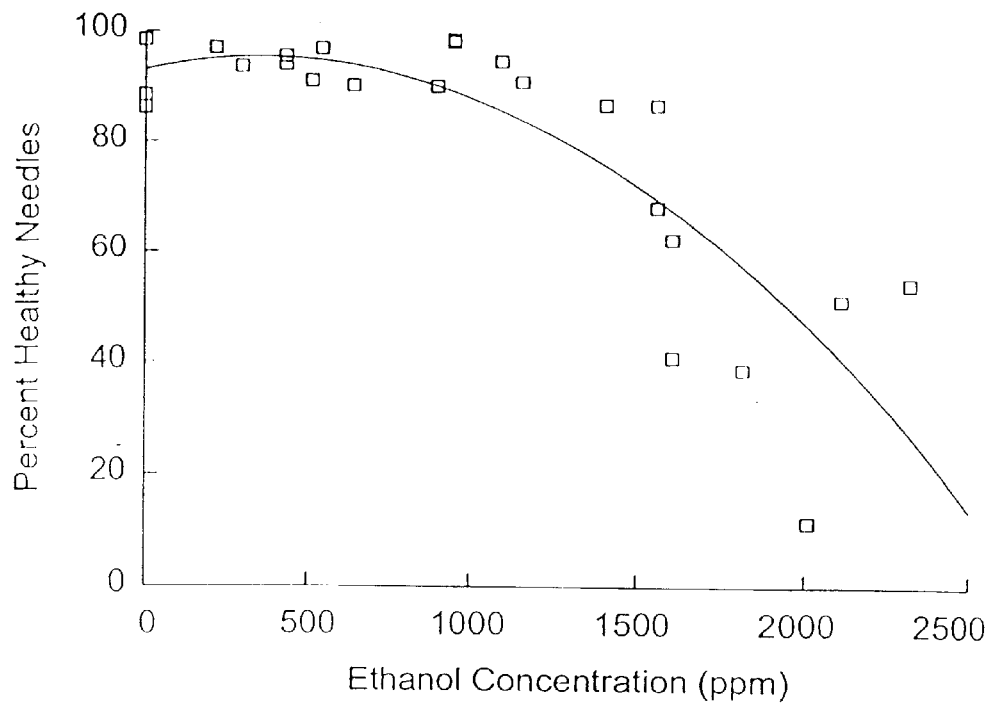
FIG. 5 is a graph showing the relationship between ethanol concentration and the percent of healthy needles for black spruce seedlings.
Figure 6:
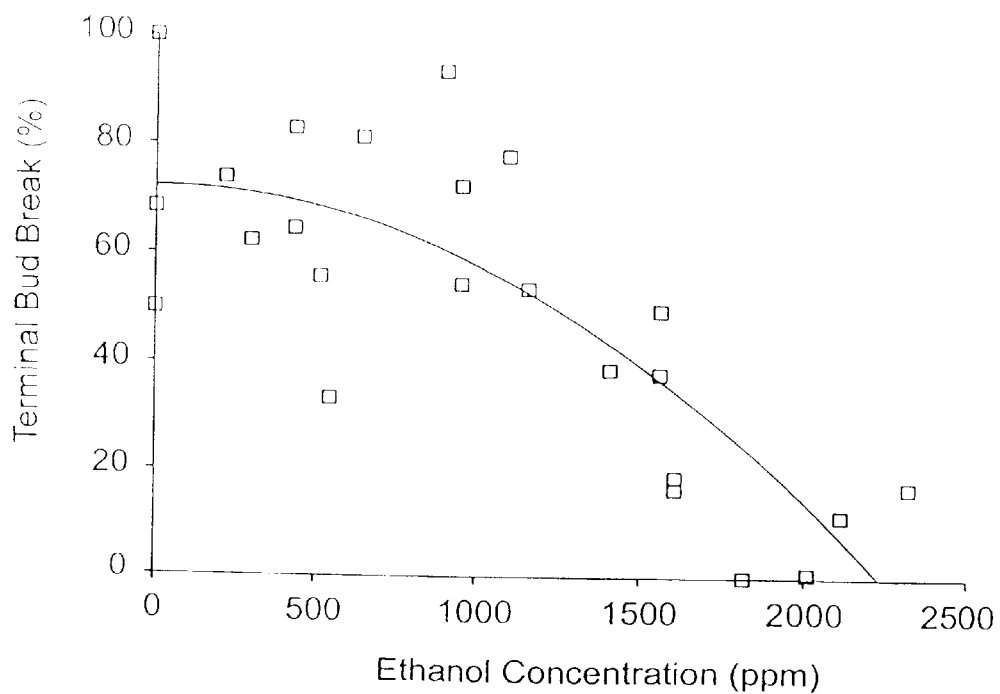
FIG. 6 is a graph showing the relationship between ethanol concentration and the percentage terminal bud break for black spruce seedlings.

Ethanol concentration in the bags from which the seedlings came was strongly correlated with growth and damage of black spruce seedlings as shown in Table 1 and FIGS. 4, 5 and 6. FIGS. 4, 5 and 6 show the relationship between ethanol concentration in bags following heat stress and seedling viability 14 days after being stressed. In each graph, the central line is the prediction based on the regression equation and the two outer lines form the 95% confidence interval. There was a general increase in ethanol concentration with increased duration of exposure during heat treatment. Below a bag concentration of 1000 ppm ethanol the number of new roots, percent bud break and needle damage were largely unaffected. Above a threshold of approximately 1000 ppm there were decreasing numbers of new roots, fewer terminal buds resuming growth, and increasing foliage damage, with increasing bag ethanol concentrations. Buds which failed to break dormancy were found upon dissection to be damaged.

Table 1 shows the root growth potential, foliage viability and terminal bud viability in black spruce seedlings from bags of different concentrations of ethanol. Results of the regression analysis are shown in Table 2.

When bag concentrations of ethanol were 1500 ppm, the average number of new roots predicted by the statistical regression analysis was 25.8, a 41% reduction compared to the predicted value of 43.8 roots at 0 ppm ethanol. Furthermore, predicted terminal bud viability decreased from an estimated value of 73.3% to 39.4% respectively at 0 ppm and 1500 ppm ethanol. Finally, predicted values of foliage viability dropped from 93.5% in the control to 72.1% at 1500 ppm. Above bag ethanol concentrations of approximately 2000 ppm seedling root growth potential and terminal bud viability decreased to near zero.

Example 2

Analysis of Stress-Induced White Spruce Seedling Damage

Plant Material

Three seed sources of operationally produced white spruce seedling (*Picea glauca*) stock were used in this experiment: site region 6276041 (Hills 1960) from Orono Nursery (48° 58' N. 78° 37' W.), fall-lifted Oct. 27, 1993, and overwintered in frozen storage at −2° C., site region 3234000 from Swastika Nursery (48° 02' N. 80° 22' W.), spring-lifted May 17, 1994, and cool stored at +2 to +3° C., and site region 4315002 from Dryden Nursery (49° 47' N. 92° 36' W.), fall-lifted Oct. 21, 1993, and overwintered in frozen storage at −2° C. The first two seed sources were grown as three-year-old seedling stock (3+0), the third source was grown as a greenhouse transplant (G+11/2) crop. Frozen stored seedlings were transported to the Ontario Forest Research Institute (OFRI) (46° 30' N. 84° 18' W.) and held at −2° C., then thawed at +2° C. for 10 days prior to treatment.

Seedling Handling

Storage treatments simulated operational conditions in the field, where bags of seedlings may be exposed to elevated temperatures for several days prior to planting. Forty seedlings per treatment were sealed in 4 mil 45 cm×80 cm polyethylene bags with excess air removed prior to dark storage for durations of 0, 8, 24, 32, 48, 56, 72 or 80 hours at 30° C. In this experiment an experimental unit was defined as a bag of seedlings containing 40 seedlings. Three replications per seed source were treated.

After a storage treatment was completed each bag of seedlings was opened and filled with air in an effort to prevent anaerobic conditions from developing during incubation. This would simulate field conditions where bags of seedlings would be opened to collect samples for incubation prior to gas analysis. The ratio of plant material to air volume inside the bag has an influence on the gas concentration measured after incubation. Therefore attempts were made to maintain a constant plant material to air ratio. The bags were then incubated in the dark for 24 hours at 20° C. After incubation the internal bag temperature was monitored with a soil probe thermometer, and, if it was 20° C. (±1° C.), a gas sample was extracted and analyzed.

Stress-Induced Gas Analysis

The concentrations of ethanol and aldehydes produced in bags by seedlings was measured using a portable gas detection system (Gastec Corp., Tokyo, Japan). The gas detection tubes are calibrated during manufacture using a combination of dynamic diffusion and gas chromatographic techniques, to ensure accurate gas concentration measurements. Gas concentrations were estimated 3 to 5 minutes after the completion of gas sampling by observing the position of the colour change in the gas detection tube.

Analysis of Stress-Induced Seedling Damage

Twenty randomly selected seedlings from each bag were removed immediately following gas extraction. Two seedlings were planted in each of 10, 3 liter pots, using a 2:1 (v:v) peat:vermiculite substrate, watered and placed into a controlled environment (26° C./18° C. day/night, 70% RH, 250 $\mu$mol m$^{-2}$ s$^{-1}$ PPFD) to allow damage symptoms to develop and growth to occur.

After 14 days, the seedlings were examined to determine root viability, terminal bud viability and foliage viability. Root systems were determined to be viable if one or more white roots were present. Terminal buds which failed to break were dissected and examined for viability. A bud was deemed to be viable if the needle primordia were green. Each seedling was visually assessed to classify damaged and undamaged needles in 10% classes.

The terminal 2 cm of the shoots of 10 randomly selected seedlings for each treatment were removed and placed in test tubes containing 30 ml distilled water. The shoot tips were incubated for 20–24 hours at 20° C., then the electrical conductivity (EC initial) of the solution was measured using a conductivity meter. Shoot tips were killed in a 90° C. oven for 3 hours, reincubated for 20–24 hours at 20° C., and the electrical conductivity (EC killed) was remeasured. The percent relative conductivity was calculated as initial conductivity×100/killed conductivity. Relative conductivity was used as an indicator of cellular membrane damage.

Chlorophyll fluorescence fv/fmax was measured on ten potted seedlings (one seedling per pot), after 48 hours of growth in the environmental chamber. Needles near the top, middle and bottom of the seedling were measured using a PAM 2000 fluorometer (Heinz Waltz GmbH, Effeltrich, Germany). The three measurements were averaged to estimate fluorescence fv/fmax for each plant.

Root, bud and foliage viability were plotted against storage treatment duration (0,8,24,32,48,56,72, or 80 hours), and compared using analysis of variance (ANOVA). Sources of variation in the ANOVA model included treatment and nursery (source). Sources were combined to compare gas emissions (ethanol and aldehydes) with treatment duration using linear regression. Root, bud and foliage viability were plotted against ethanol and concentration of aldehydes. Root, bud and foliage viability were plotted against chlorophyll fluorescence fv/fmax (optimum quantum yield) and relative conductivity and best fit linear or polynomial regressions were calculated.

Correlations between root, bud, and foliage viability and duration of warm storage were significant (Table 5). Increasing warm storage duration significantly reduced root, bud and foliage viability. Since the primary source of variation was found to be the treatment durations all sources were combined for subsequent linear regression. The correlation between ethanol concentration and warm storage treatment duration was significant ($r^2$=0.52). The relationship between concentration of aldehydes and treatment duration was even stronger ($r^2$=0.76).

Correlations of ethanol and aldehyde concentration with root, bud, and foliage viability were also significant (Table 5). In general, at low ethanol concentrations (less than 300 ppm) and low concentrations of aldehydes (less than 20 ppm) the viability of different parts of the plant remained high (FIGS. 7–12). At ethanol concentrations from 400–1200 ppm and aldehyde concentrations from 20 to 30 ppm the viability of different parts of the plant was variable; some seedlings had low levels of damage, while others were severely damaged. Ethanol concentrations greater than 1200 ppm and concentrations of aldehydes greater than 30 ppm were associated with poor viability in all attributes measured (FIGS. 7–12).

Correlation between root, bud, foliage viability and chlorophyll fluorescence fv/fmax were strong (Table 5). The linear regression between chlorophyll fluorescence yield and foliage viability was very strong ($r^2$=0.94). Foliar relative conductively was less well correlated with any subsequent measure of viability (Table 5).

A significant relationship was found between bag concentrations of ethanol and root, bud and foliage viability, as shown in FIGS. 7, 8 and 9 respectively. A significant relationship was also found between bag concentrations of aldehydes and root, bud and foliage viability, as shown in FIGS. 10, 11 and 12 respectively. The error bars in FIGS. 7–12 show the 95% confidence interval. Tables 3 and 4 show the correlation between concentration of ethanol and aldehydes respectively, and root, bud and foliage viability.

In general, at low ethanol concentrations (less than 400 ppm) and low aldehyde concentrations (less than 20 ppm) the viability of the different parts of the plants remains high. At ethanol concentrations from 400–1200 ppm and aldehydes concentrations from 20 to 30 ppm the average viability is reduced as some seedlings have low levels of damage, while others are severely damaged. Ethanol concentrations greater than 1200 ppm or aldehyde concentrations greater than 30 ppm were associated with poor viability in all attributes measured. The results of the regression analysis is set out in Table 5 which shows the correlation between root, bud and foliage viability and the various methods of estimating plant quality.

The information in Table 2 may be used, for example, to determine root viability for this species based on ethanol measurement, using the equation y=−0.06x+70.87, where x is the measure of ethanol concentration. For example, if the measured concentration was 600 ppm, then y=−0.06(600)+70.87; or y=34.87%. Thus about 34% of the seedlings will have viable root systems at an ethanol concentration of 600 ppm.

Based on the results, white spruce seedlings may be classified as follows: undamaged seedlings, have an ethanol measurement less than 400 ppm and an aldehyde measurement less than 20 ppm; damaged seedlings have an ethanol measurement of from 400 to 1200 ppm and an aldehyde measurement of from 20–30 ppm and; severely damaged (non-viable) seedlings have an ethanol measurement over 1200 ppm or an aldehyde measurement greater than 30 ppm.

The results show that seedlings exposed to elevated temperatures while packaged in polyethylene lined kraft paper bags may be severely damaged in relatively short periods of time. For, example in as little as 48 hours, root viability may drop from near 100% to an average of 19.3%. The lack of difference between stocklots in this study indicates that the prediction of damage and viability using the methods of the invention is independent of seedlot and cultural factors.

The correlations between duration of warm storage and gas emissions were very strong. However, under operational conditions storage temperatures and duration are seldom accurately known. Furthermore, storage temperature is an environmental factor which may or may not cause seedling damage. Seedling stress resistance depends on factors of stress avoidance and tolerance. For this reason, except in extreme cases monitoring temperature conditions inside packages of seedlings has limited operational value in predicting seedling condition at the planting site.

Ethanol and aldehyde emissions were both good indicators of seedling viability following storage at 30° C. When a multiple linear regression model was tested, the analysis indicated that both parameters are approximately equal in terms of predictive ability and that a model combining both factors would be no more predictive than a model using either factor individually. Simple linear regression models were computed for each gas and viability parameter (Table 5). At low ethanol (less than 400 ppm) and aldehydes (less than 20 ppm) concentrations, seedling viability was not appreciably different from the control. At concentrations, between 400 and 1200 ppm ethanol and 20 to 40 ppm aldehydes, the viability of the stock was variable, with some samples performing well, while other samples performed very poorly. However, at ethanol concentrations greater than 1200 ppm and aldehyde concentrations greater than 40 ppm, very poor seedling viability was reliably predicted using the methods of the invention.

Example 3

Field Trials

The methods described above have been used to assess nursery stock shipments of black spruce seedlings under normal field conditions. Damage was suspected in a nursery stock lot of approximately 70,000 seedlings as the seedlings were thought to have been stored at an elevated temperature, although no visual symptoms of damage were apparent. A random sampling of gas from several bags found ethanol levels ranging from 1800 to 2500 ppm. Based on these results, shipment of the stock was delayed to allow further evaluation of the stock.

The results obtained were confirmed by planting a sample of the seedlings and assessing viability of the plants by measuring root growth capacity, relative conductivity and chlorophyll fluorescence following the methods described above. These measurements confirmed that the high ethanol levels had correctly identified non-viable stock with a high level of damage, which would have failed if planted. The rapid identification of the damaged stock permitted healthy replacement seedlings to be planted in place of the damaged stock, which was discarded.

Example 4

Detection of Stress-Induced Damage to Fruit Using Gas Analysis

Plant Material and Stress Treatment

The effects of stress on the production and measurement of gases produced by fruit were measured using bananas (Musa spp.). Bananas were obtained from a commercial supplier and averaged approximately 20 cm in length and 3.5 cm diameter. At the time of use the peel of the bananas was uniformly yellow without brown spots.

One bunch of five bananas was sealed in each of 5 polyethylene bags, each bunch being of approximately the same weight. A range of levels of fruit stress was created by dropping the bags of bananas from a height of 1 meter onto a table 0, 1, 2, 4 or 8 drops. After dropping, the bags of bananas were placed in a growth chamber at 25° C. to allow gases to collect inside the sealed bags. After 24 h in the growth chamber, ethanol and acetaldehyde gas measurements for each of the bags were made using a portable gas analysis system.

Stress-Induced Gas Analysis

Ethanol and acetaldehyde gas samples were collected as follows. A gas detection tube was attached to the vacuum pump and inserted approximately 6 cm into a 1 mm diameter hole in the bag containing the bananas. The vacuum pump was manually operated to withdraw 100 $cm^3$ of gases from the bag through a ethanol gas detector tube for ethanol and 400 $cm^3$ through a acetaldehyde detector tube. After sampling was complete the tubes were removed from the bags. Gas concentration was estimated after a further five minutes by observing the position of the color change in the gas detector tubes.

Detection of Stress-Induced Damage to Bananas

After 4 days the bananas were examined to determine the extent of bruising. Bruises were identified on the surface of the peel and to the fruit inside after removing the peel. The relationship between dropping and gas concentration was analysed using analysis of variance to compare dropped versus non-dropped fruit.

Figure 13:
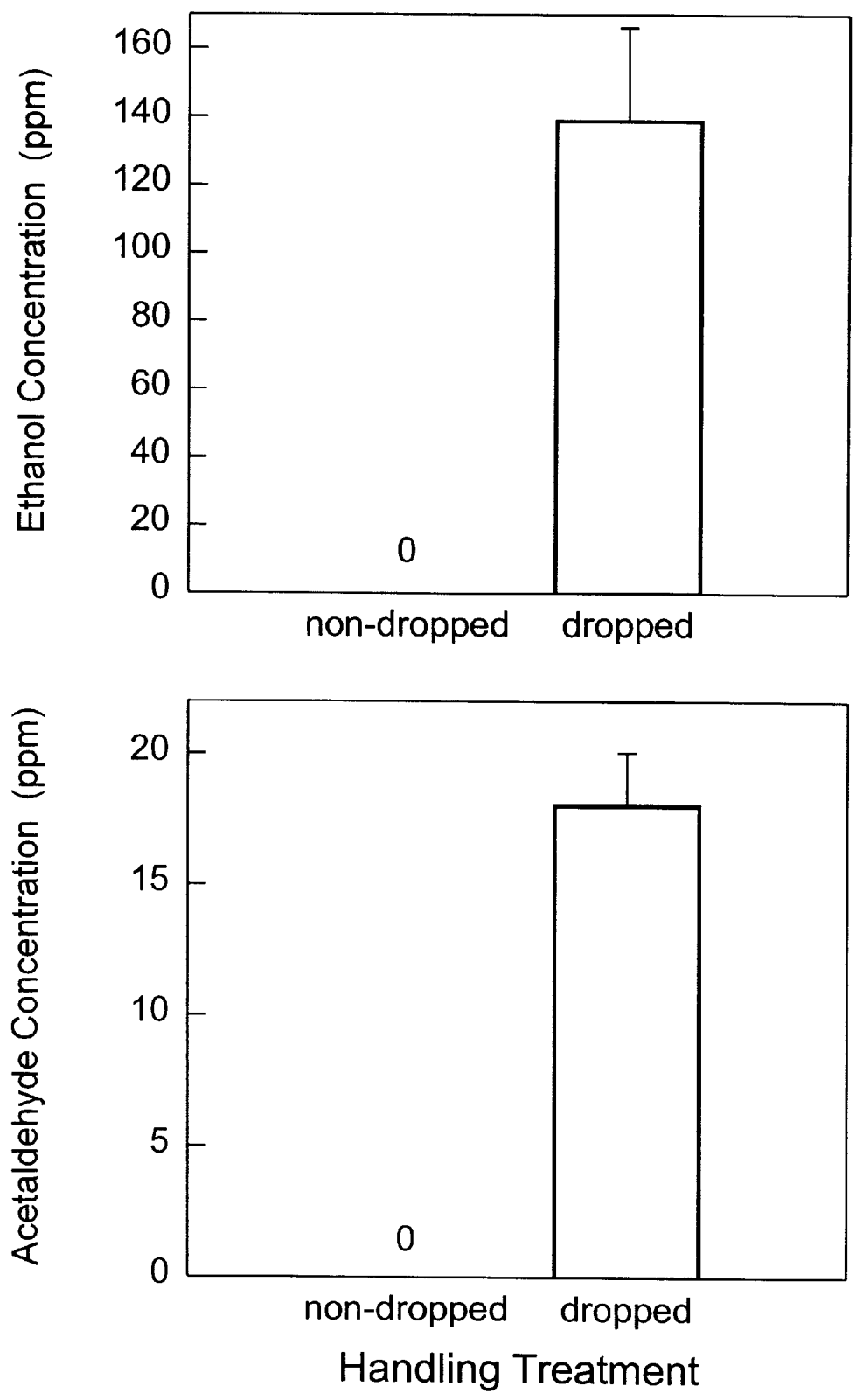
FIG. 13 are graphs showing the effect of dropping on the production of volatile emissions by bananas.

Ethanol and acetaldehyde concentrations in the bags from which the bananas came were strongly correlated with dropping. As shown in FIG. 13, fruit that was not dropped produced neither ethanol or acetaldehyde. In contrast, fruit dropped once or more produced on average 139 ppm ethanol and 18 ppm acetaldehyde. One drop caused the fruit to produce the same amount of ethanol and acetaldehyde as fruit dropped up to eight times.

Immediately after dropping there was no external visual evidence of damage to the dropped or non-dropped fruit. Four days after treatment, there was still no evidence of bruising of the peel and pulp of the banana fruit that was not dropped. In comparison, fruit dropped once or more was bruised over an area of approximately 20 $cm^2$ on the basal portion of each of the 3 bananas on the bottom of each bunch.

These results demonstrate the ability of the invention to detect the condition of a fruit when non-visual damage is present. The invention was highly successful in grouping the fruit into categories of damaged and non-damaged. The absence of increased gas concentrations or damage with increased amount of dropping is attributed to the fact that the contact surface of the fruit was the same regardless of the number of times it was dropped (i.e., approximately 20 $cm^3$ on the basal portion of each of the 3 bananas on the bottom of each bunch was affected regardless of the number of times the fruit was dropped).

Example 5

Evaluation of Fruit Ripening Using Gas Analysis

Plant Material

Bananas usually are harvested at a hard green stage and complete their ripening after shipment (Thompson and Seymour 1982). Ethylene production and ripening of fruit are related (Liu 1976, Beaudry et al. 1987). For this reason, ethylene is used commercially to induce ripening (Saltveit et al. 1978, Inaba and Nakamura 1988). Practical methods for measuring ethylene and other gases related to fruit condition are not available. We investigated the use of the portable gas measurement system to evaluate gases produced by ripening bananas (Musa spp.). The application of this technique holds promise as a means by which those involved in producing, handling and retailing fruit can evaluate the stage of ripening of their product.

Green bananas were obtained from a commercial supplier and averaged approximately 20 cm in length and 3.5 cm diameter. Gases produced by bananas were analyzed at different stages of ripening as indicated by color of the fruit. Six color stages were visually identified: green, green/yellow, yellow/green, yellow, yellow/brown, and brown. At each stage of ripening two bunches of five bananas were sealed in polyethylene bags. The bags of bananas were placed in a growth chamber at 25° C. to allow gases to collect inside the sealed bags. After 24 h in the growth chamber, the gases in each bag were assessed using a portable gas analysis system to detect ethanol, acetaldehyde and ethylene.

Gas Analysis

Gas samples were collected as follows. A gas detection tube was attached to the vacuum pump and inserted approximately 6 cm into a 1 mm diameter hole in the bag containing the bananas. The vacuum pump was manually operated to withdraw 100 cm$^3$ of gases from the bag through an ethanol gas detector tube for ethanol, and 400 cm$^3$ through acetaldehyde and ethylene detector tubes. After sampling was complete the tubes were removed from the bags of bananas. Gas concentrations were estimated after a further five minutes by observing the position of the color change in the gas detector tubes.

Relationship Between Ripening and Gas Production

Figure 14:
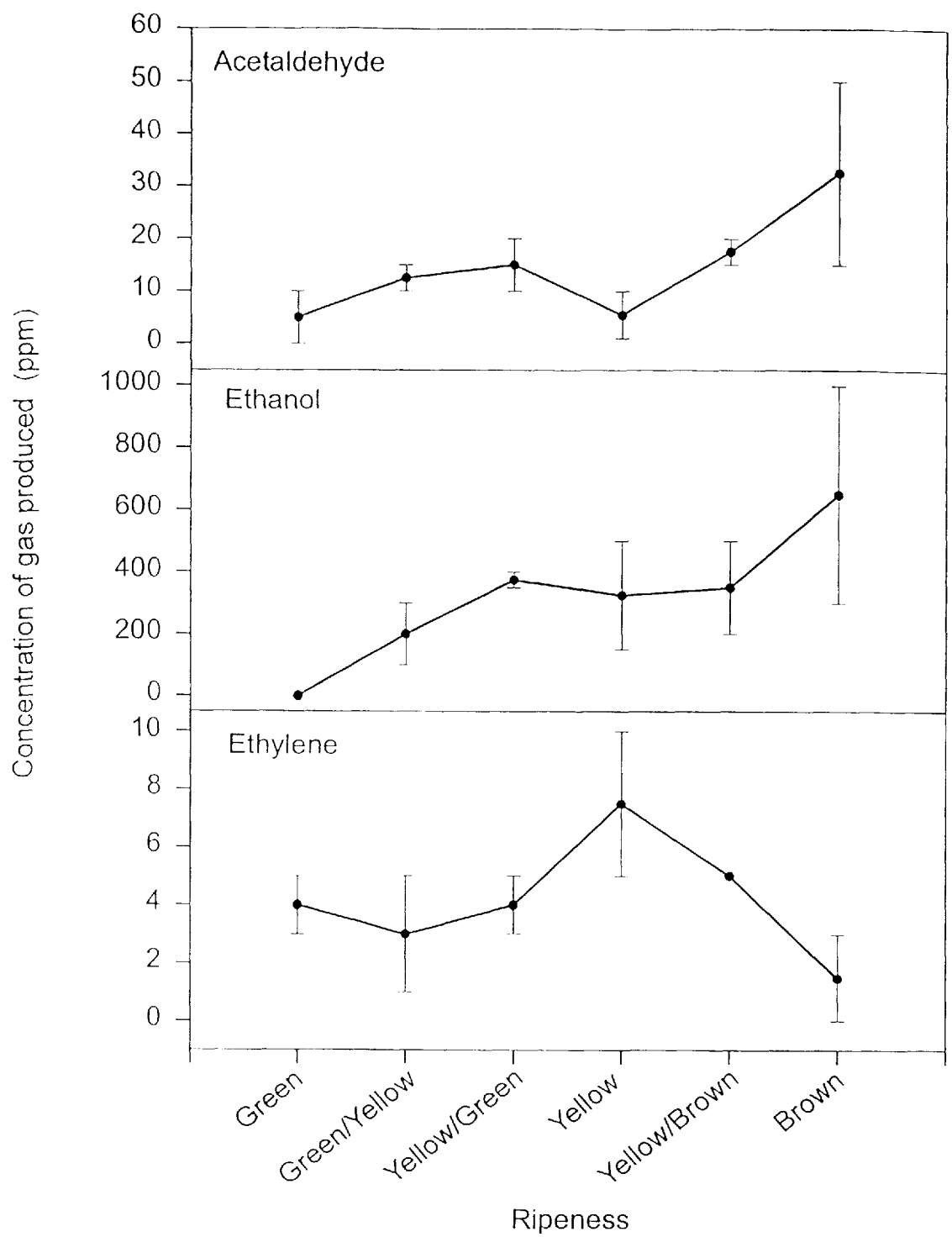
FIG. 14 are graphs showing the production of acetaldehyde, ethanol, and ethylene gases by banana (*Musa sativa*) at different stages of ripening.

The amount of each of the measured gases varied according to a different pattern during ripening (FIG. 14). The production of acetaldehyde was lowest when bananas were green. When the bananas were green to yellow/brown in color the concentration of acetaldehyde varied between 5 and 15 ppm. However, as the bananas turned brown the production of acetaldehyde increased, reaching a maximum of over 30 ppm. In contrast, ethanol production increased from 0 ppm in green bananas to a plateau of between 250 and 375 ppm when color ranged from yellow/green to yellow/brown. Highest ethanol production occurred for brown bananas, with a concentration of over 600 ppm.

In comparison, the production of ethylene peaked when bananas were yellow (7.5 ppm), after which ethylene production fell to a minimum of only 1.5 ppm in brown bananas. The concentration of ethylene measured using the portable gas measurement system compared well to concentrations reported in the literature where measurement was by means of gas chromatography (Beaudry et al. 1987). In addition, using the portable gas measurement system the climacteric production of ethylene was detected (i.e. climacteric refers to the rise in respiration and ethylene production associated with full ripeness of many fruits). These result indicate the suitability of the invention to monitor the condition of fruit relative to stage of ripening.

References

Beaudry, R. M., Pas, N., Black, C. C. and Kays, S. J. 1987. Banana ripening: Implications of changes in internal ethylene and CO$_2$ concentrations, pulp fructose 2,6-biphosphate concentration, and activity of some glycolytic enzymes. Plant Physiol. 85: 277–282.

Inaba, A. and Nakamura, R. 1988. Numerical expression for estimating the minimum ethylene exposure time necessary to induce ripening in banana fruit. J. Amer. Soc. Hort. Sci. 113: 561–564.

Liu, F. W. 1976. Correlation between banana storage life and minimum time required for ethylene response. J. Amer. Soc. Hort. Sci. 101: 63–65.

Saltveit, M. E. Jr., Bradford, K. J. and Dilley, D. R. 1978. Silver ion inhibits ethylene synthesis and action in ripening fruits. J. Amer. Soc. Hort. Sci. 103: 472–475.

Thompson, A. K. and Seymour, G. B. 1982. Comparative effects of acetylene gas on initiation of banana ripening. Ann. Appl. Biol. 101: 407–410.

Example 6

Detection of Stress-Induced Damage to Vegetables Using Gas Analysis

Plant Material and Stress Treatment

The effects of stress on the production and measurement of gases produced by vegetables was measured using broccoli (Brassica oleracea). "Bunches" of broccoli obtained from a commercial supplier averaged approximately 25 cm in length and ranged in fresh weight from 311 to 621 g. At the time of use the broccoli was dark green in color and the flower heads in the bunches were tight (i.e. firm to touch).

One bunch of broccoli was sealed in each of 5 polyethylene bags. A range of levels of stress was created by placing the bags of broccoli in a controlled environment chamber at 47° C., with bags being removed after different periods of exposure (this temperature is similar to that which may occur if packaged plants are left in sealed containers for extended periods). Heat treatment durations were 0, 90, 135, 180 or 225 minutes. After heating, the bags of broccoli were placed in a growth chamber at 25° C. to allow gases to collect inside the sealed bags.

Stress-Induced Gas Analysis

After 24 h in the growth chamber, ethanol and acetaldehyde gas measurements of each bag were made using a portable gas analysis system. Ethanol and acetaldehyde gas samples were collected as described previously. A gas detection tube attached to the vacuum pump was inserted approximately 6 cm through a 1 mm diameter hole in the bag containing the broccoli. Using a manually operated vacuum pump 100 cm$^3$ of the gases from the bag was drawn through the ethanol gas detector tube and 400 cm$^3$ through the acetaldehyde detector tube. After sampling was complete the tubes were removed from the bags. Gas concentration was estimated after a further five minutes by observing the position of the color change in the gas detector tubes.

Detection of Stress-Induced Damage to Broccoli

After gases were measured the bags were opened and approximately 5 g fresh weight of tissue from the flower heads was excised, placed in test tubes, and covered with distilled water to measure the post-stress leakage of electrolytes. A high amount of electrolyte leakage measures damage by identifying the loss of semi-permeability of the cell membranes of the tissue.

The excised tissue samples were incubated for 20–24 hours at 20° C. prior to measuring electrical conductivity of the bathing solution (EC initial). After the initial measurement the test tubes were placed in an oven at 70° C. for 3 hours to completely kill the tissues and release the total cell electrolyte contents. A measurement of the electrical conductivity (EC killed) was taken after a further 20–24 hours incubation at 20° C. The percent relative conductivity was calculated as: EC initial×100/EC killed.

After measuring gas concentrations and collecting samples to assess electrolyte leakage, the bunches of broccoli were removed from the bags and placed with the lower, cut ends of the stems in water. Four days later the broccoli was examined to identify damage based on the change in color and loss of head tightness. The color of each bunch of broccoli was rated as dark green, olive green, or yellow. Flowers on the heads were rated as either turgid (in which the florets are compact, close together and hard to the touch), or flaccid (where the florets are drooping and loose to the touch). The relationship between damage (measured by relative conductivity or visual signs) and gas concentration was analyzed using linear and non-linear regression. The results of three trials conducted at different times were combined.

Heating broccoli for up to 135 minutes at 47° C. resulted in no immediate visual evidence of damage. When heated for 180 minutes or longer the color changed from dark green to olive green immediately after treatment and there was also slight flaccidity.

Figure 15:
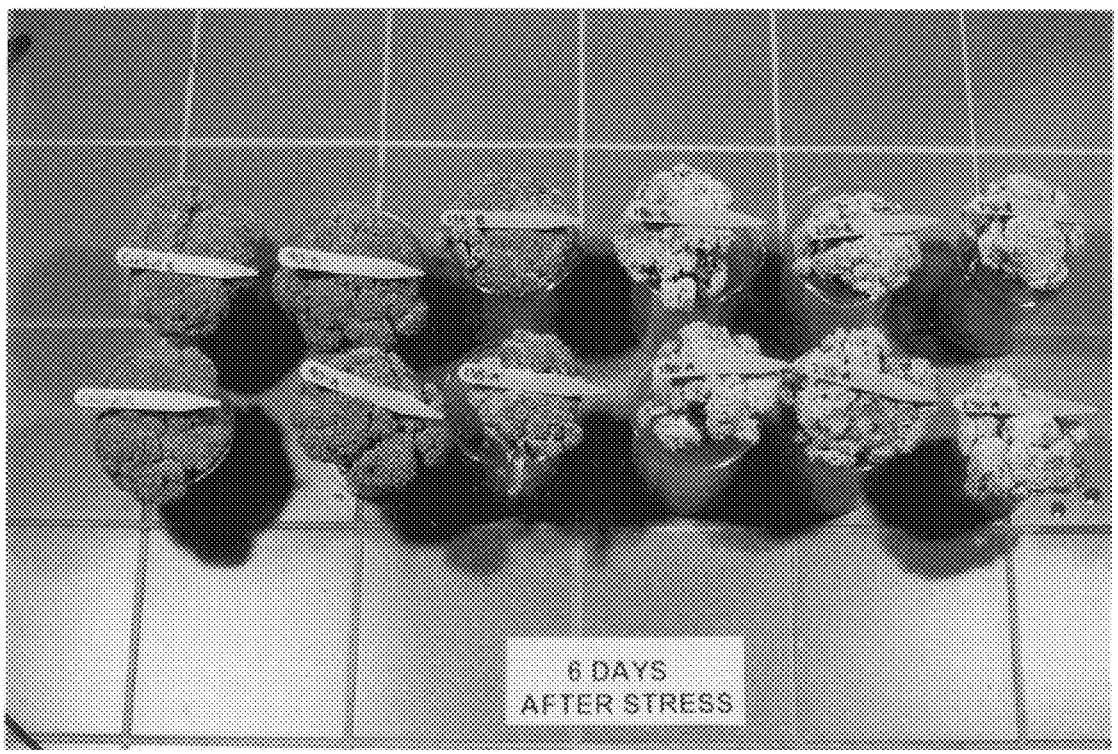
FIG. 15 is a photograph showing the effect of heating on broccoli color and head tightness.

Six days after treatment there was evidence of color change and loss of head tightness as a result of heating for 90 minutes or longer (FIG. 15). Without heating neither ethanol or acetaldehyde were produced and after four days the broccoli was olive green in colour and the florest were turgid. With 90 and 135 minutes of heating ethanol and acetaldehyde were respectively 25–400 ppm and 0.5–6.8 ppm, while the color of the broccoli was also olive green and the florets were flaccid after four days. When heated for 180 minutes or longer the broccoli produced between 450 and 700 ppm ethanol and 15 to 60 ppm acetaldehyde, while the color turned yellow and the florets became flaccid.

Figure 16:
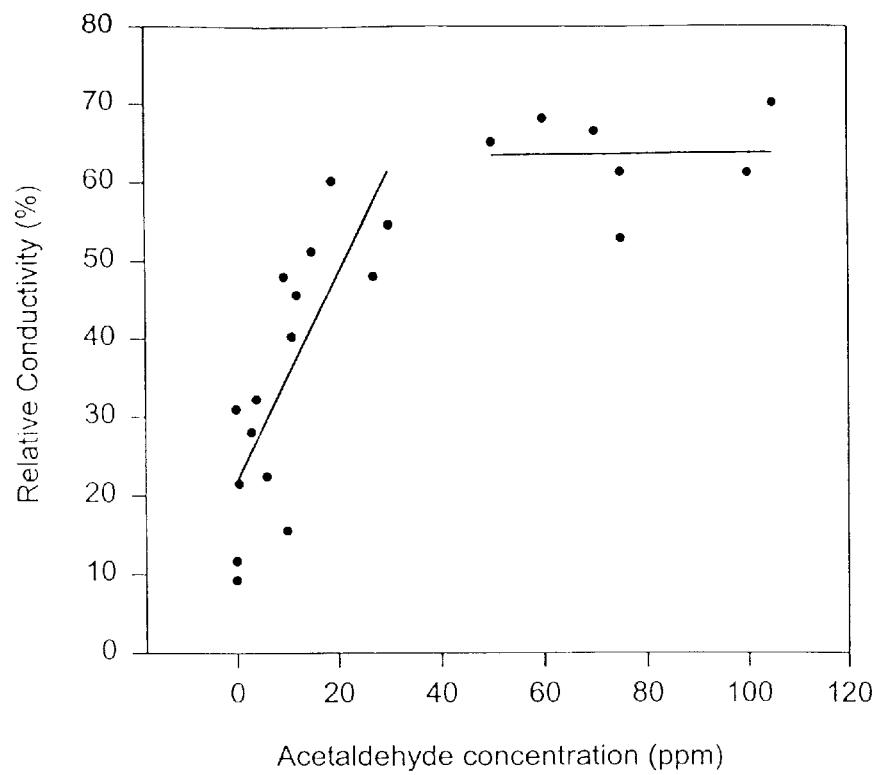
FIG. 16 is a graph showing the effect of heating on the production of acetaldehyde by broccoli.
Figure 17:
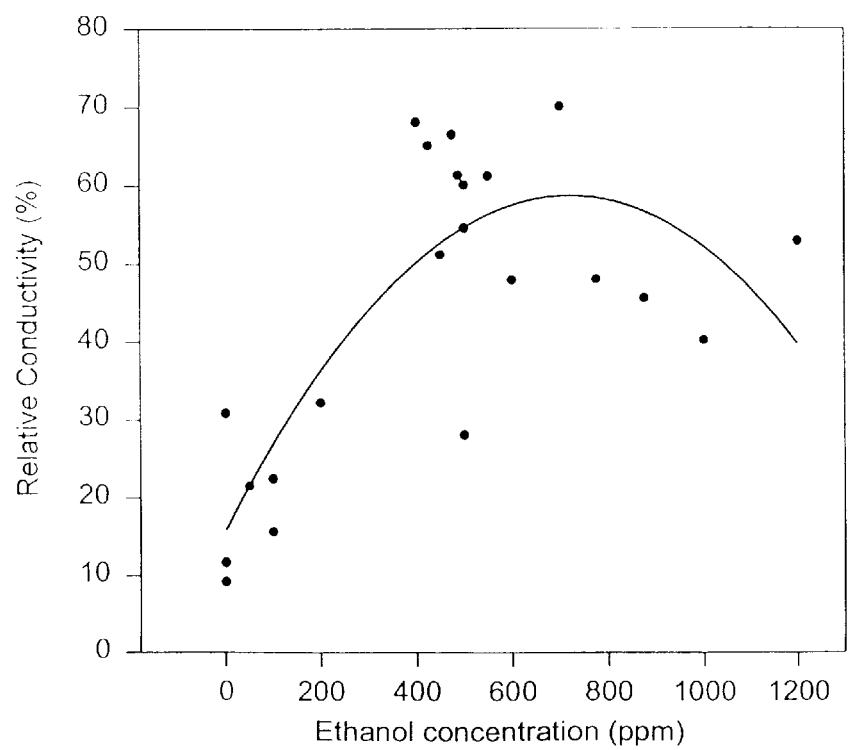
FIG. 17 is a graph showing the effect of heating on the production of ethanol by broccoli.

Relative conductivity of the leachate from broccoli florets increased from <10% in non-heated tissues to over 70% with heating for 270 minutes. Acetaldehyde concentrations produced following heating were strongly correlated with the amount of damage measured by relative conductivity. As shown in FIG. 16, broccoli producing low amounts of acetaldehyde also had low relative conductivity, and as the concentration of acetaldehyde increased there was a linear increase in damage (measured by relative conductivity). When acetaldehyde concentrations exceeded 40 ppm relative conductivity reached a maximum value of about 60%. Relative conductivity also increased with the concentration of ethanol produced by broccoli (FIG. 17). In comparison to acetaldehyde, there was a parabolic relationship between relative conductivity and ethanol produced.

These results demonstrate the ability of the invention to detect the condition of a vegetable when non-visual damage is present. The invention was highly successful in grading broccoli according to the amount of damage caused by a heat stress based on the production of acetaldehyde and ethanol gases.

Example 7

Detection of Stress-Induced Damage to Flowers Using Gas Analysis

Plant Material and Stress Treatment

The life of cut flowers can be shortened by exposure to environmental stresses such as drying and heat. As for other types of plants, it can be hypothesized that a stress that causes damage may be detected through the measurement of volatile compounds. To test this hypothesis, the effects of a heat stress on the production and measurement of gases produced by cut flowers was measured using Chrysanthemum (*Dendranthema rubellum*). The stems of cut flowers obtained from a commercial supplier averaged approximately 45 cm in length and the flowers were fully expanded.

Ten flowers were sealed in each of 5 polyethylene bags. A range of levels of stress was created by placing the bags of flowers in a controlled environment chamber at 47° C., with bags being removed at different times. After heating, the bags of flowers were placed in a growth chamber at 25° C. to allow gases to collect inside the sealed bags to accumulate.

Stress-Induced Gas Analysis

After 24 h in the growth chamber, ethanol and acetaldehyde gas measurement of each bag was made using a portable gas analysis system. Ethanol and acetaldehyde gas samples were collected as described previously. A gas detection tube attached to the vacuum pump was inserted approximately 6 cm through a 1 mm diameter hole in the bag containing the broccoli. Using the vacuum pump 100 $cm^3$ of the gases from the bag was drawn through the ethanol gas detector tube and 400 $cm^3$ through the acetaldehyde detector tube. After sampling was complete the tubes were removed from the bags. Gas concentration was estimated after a further five minutes by observing the position of the color change in the gas detector tubes.

Detection of Stress-Induced Damage to Chrysanthemum

After measuring acetaldehyde and ethanol the flowers were removed from the bags and the placed with the lower ends of the stems in water. Four days later the flowers were examined to identify damage based on the change in color and drooping of the head of the flower. The percent browning of each flower was rated. Flowers were classified as drooping or not drooping. As the occurrence of flower drooping and the incidence of flower browning were nearly identical only the results for percent browning are presented. The results of three trials conducted at different times are presented separately.

Figure 18:
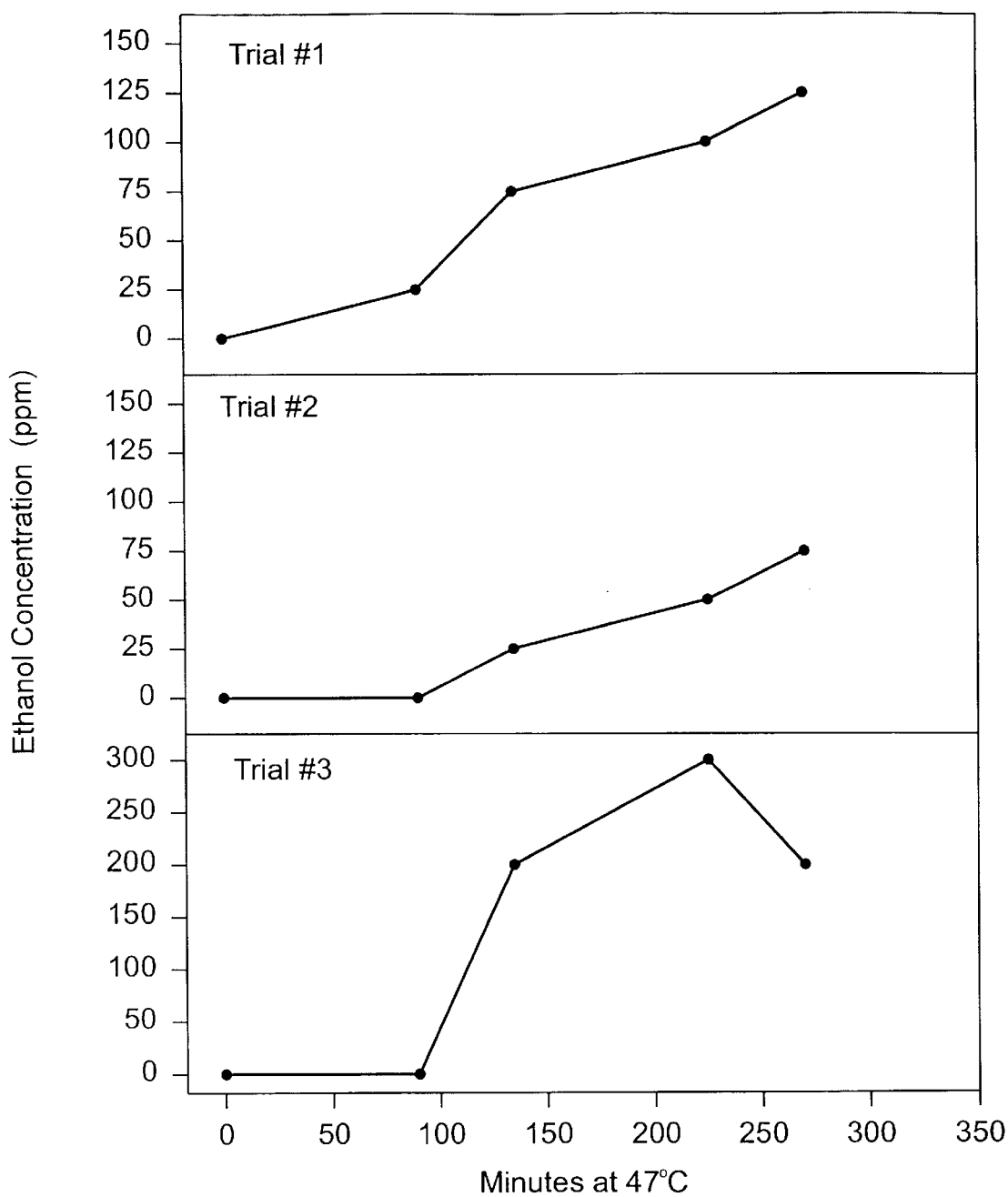
FIG. 18 are graphs showing the effect of heating on the production of ethanol gas by Chrysanthemum.
Figure 19:
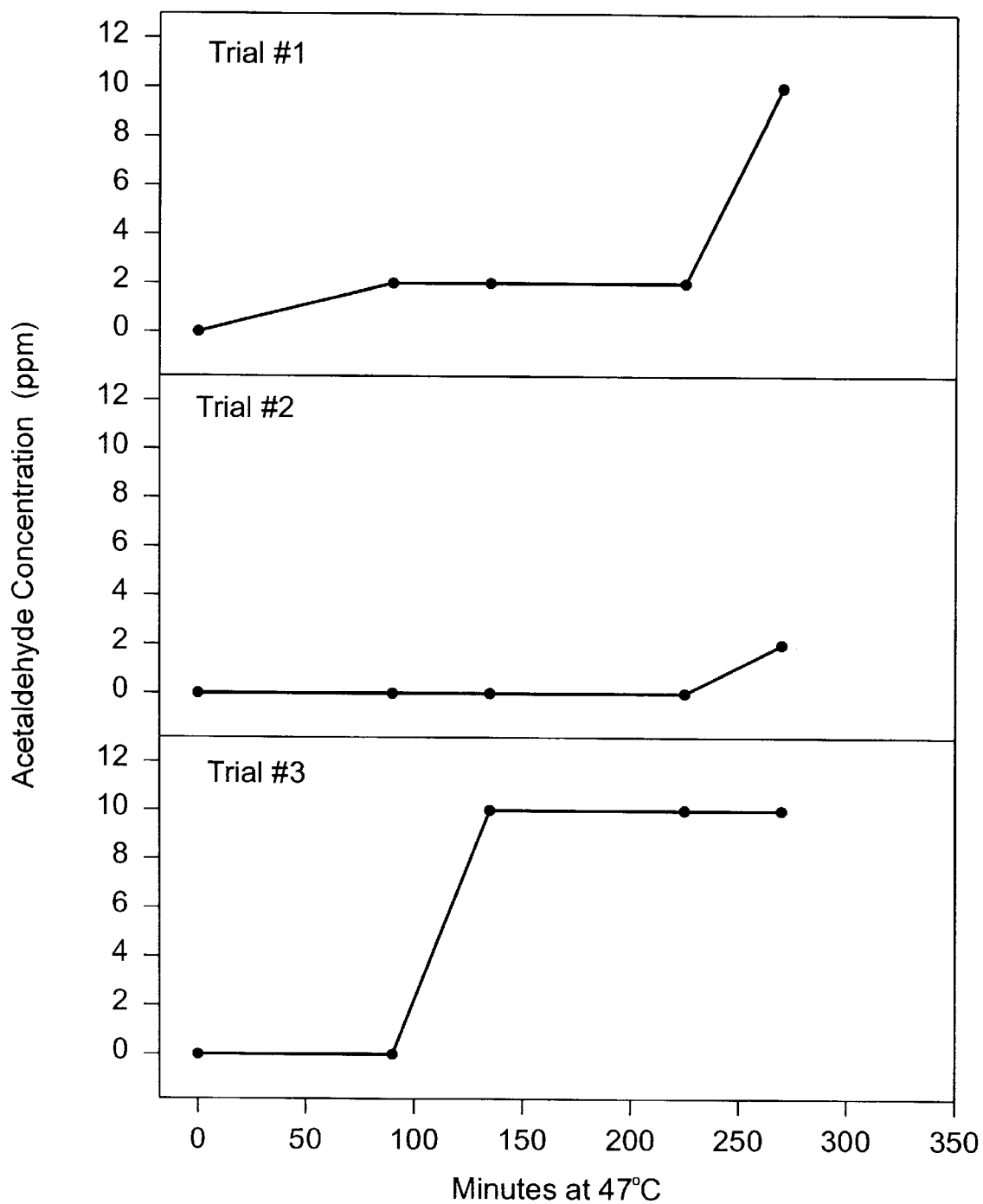
FIG. 19 are graphs showing the effect of heating on the production of acetaldehyde gas by chrysanthemum.

In Trials #1 and #2, increased duration of heating increased the production of ethanol (FIG. 18). In contrast, ethanol in Trial #3 increased according to a typical dose-response curve. The amount of acetaldehyde produced by heating likewise was unique in each trial (FIG. 19).

Figure 20:
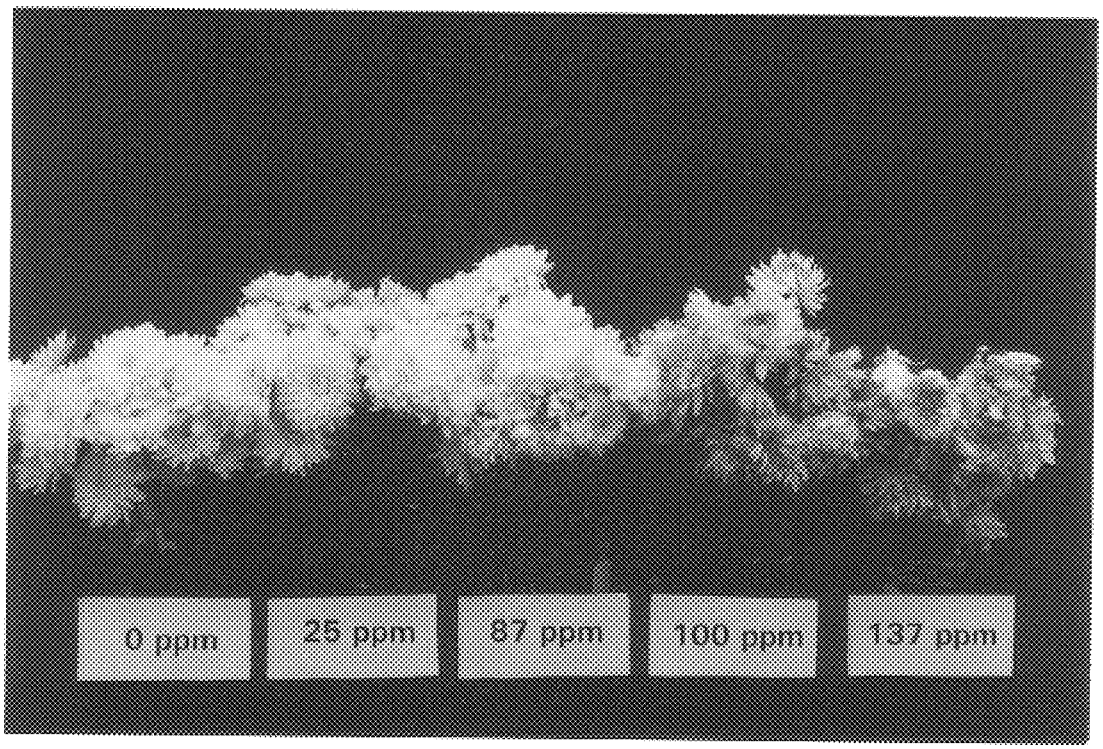
FIG. 20 is a photograph showing the relationship between ethanol gas concentration produced by Chrysanthemums and flower damage caused by heating.
Figure 21:
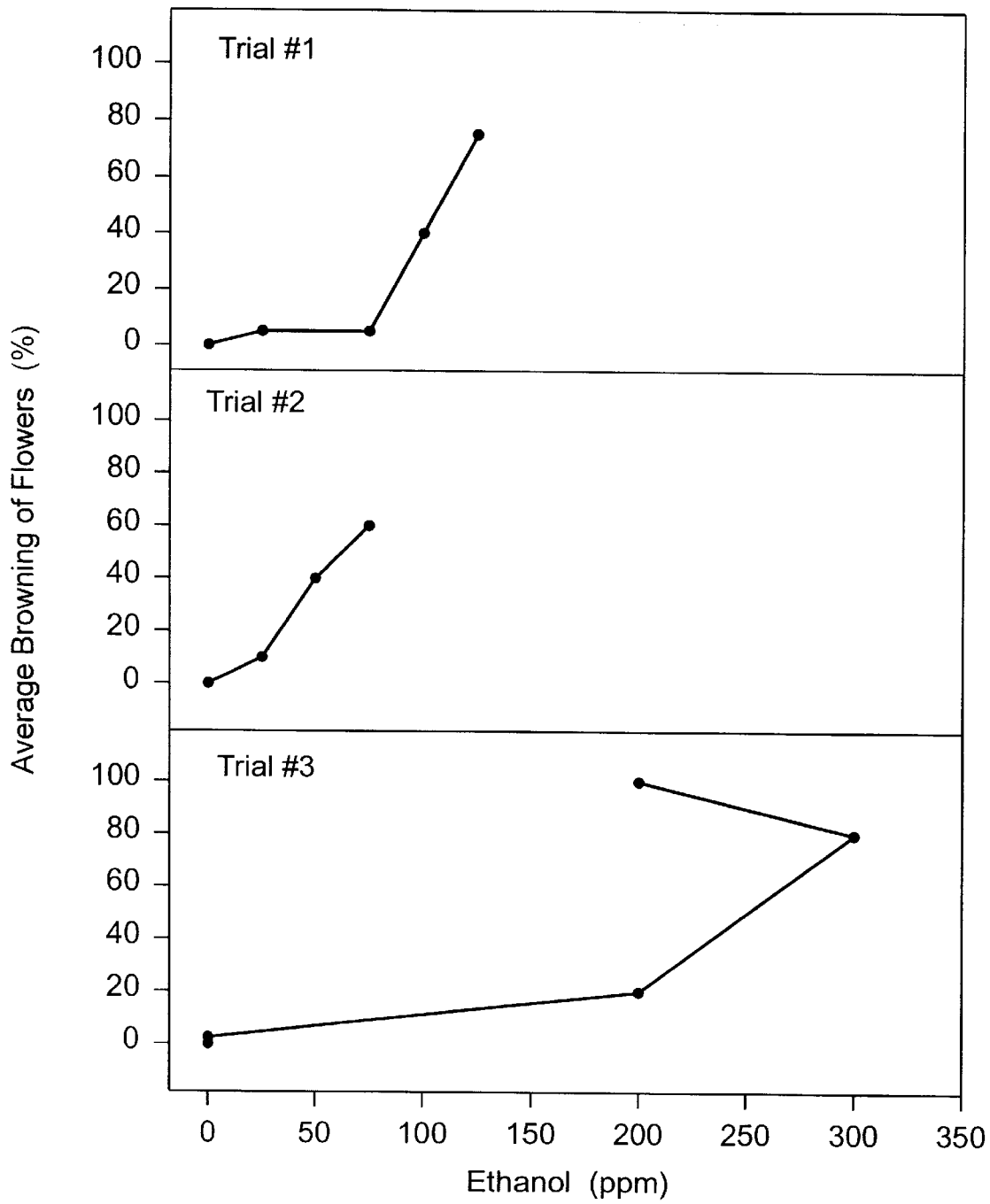
FIG. 21 are graphs showing the relationship between ethanol production and flower browning in Chrysanthemum.
Figure 22:
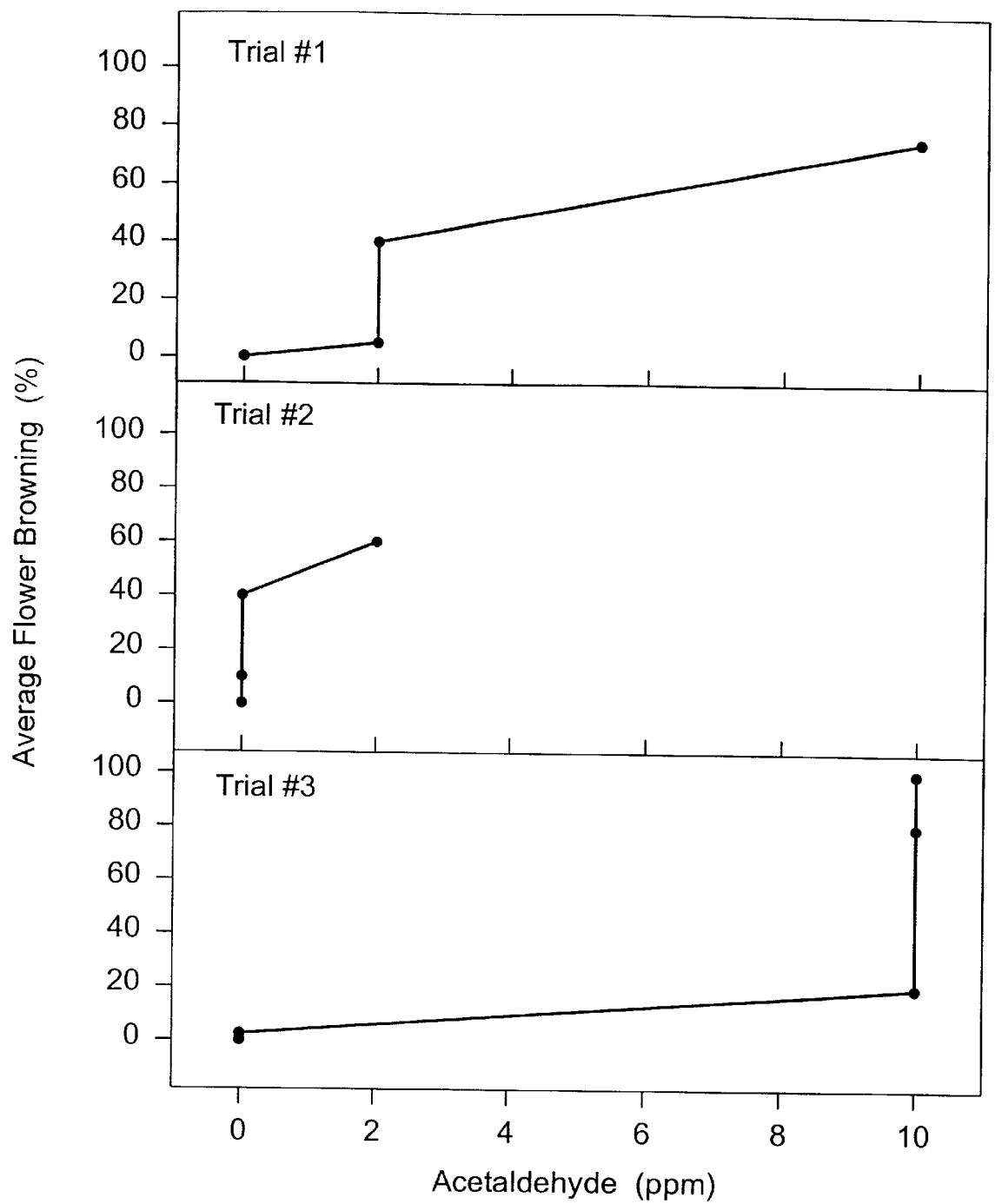
FIG. 22 are graphs showing the relationship between acetaldehyde and flower browning in Chrysanthemum.

Browning was not evident when flowers were measured for ethanol and acetaldehyde production. However, four days after being stressed, flower browning was clearly evident (FIG. 20). The relationship between ethanol production and flower browning varied for each trial (FIG. 21): in trial #1, damage did not increase until an ethanol concentration of 100 ppm occurred; in trial #2, damage was evident with the production of 25 ppm ethanol; in trial #3, damage was not evident until 200 ppm ethanol was produced. In addition, when the flowers were 100% damaged in Trial #3 the amount of ethanol produced was reduced. The concentration of acetaldehyde gas produced and the amount of damage in Chrysanthemum was similarly unique in each of the trials conducted (FIG. 22). In all three trials, the highest level of acetaldehyde gas produced occurred where greater than 50% of the flowers turned brown following heating.

These results demonstrate the ability of the invention to detect the presence of damage in flowers. Tests performed at three different times provided different relationships between the amount of ethanol and acetaldehyde gases produced and the amount of damage present. Variability in response may reflect unique responses of different cultivars of Chrysanthemums in the three trials, or differences in the physiological condition of the flowers received for testing on the different dates. Regardless, in all cases, elevated levels of these gases produced prior to the onset of visual symptoms were successful in indicating damage.

Example 8

Detection of Stress-Induced Damage to Loblolly Pine Seedlings Using Gas Analysis Plant Material and Stress Treatment The effects of stress on the production and measurement of gases produced by loblolly pine (*Pinus taeda* L.) was examined using seedlings obtained from three commercial nurseries. Dormant seedlings were obtained from cold storage at the Weyerhaeuser nurseries at Washington, N.C. and Aiken, S.C., and from the International Forest Seed Company Nursery in Statesboro, Ga.

A range of levels of decreased quality of loblolly pine seedlings was created by placing trees in shipping bags in a 30° C. growth chamber for increasing periods of time. At regular intervals after being placed in 30° C., samples of seedlings were withdrawn for evaluation.

Stress-Induced Gas Analysis

Seedlings were evaluated after warm storage using stress-induced emission of ethanol and acetaldehyde gases. Gas samples were collected as follows. A gas detection tube attached to the vacuum pump was inserted approximately 6 cm into a 1 mm diameter hole in the bag containing the seedlings. The vacuum pump was manually operated to withdraw 50 cm$^3$ of gases from the bag through a gas detector tube for ethanol and 400 cm$^3$ through a detector tube for acetaldehyde. After sampling was complete the tubes were removed from the bags. Gas concentration was estimated after a further five minutes by observing the position of the color change in the gas detector tubes.

For testing ethanol gas concentrations, 100 cc. gas samples are usually drawn through the tube to obtain a reading in parts per million. Drawing larger or smaller gas samples through the tube provides a reading on the detector tube. However, the values are not true parts per million, even though the tube is graduated in parts per million scale. Because very high ethanol concentrations (>2,000 ppm) were sometimes obtained with loblolly pine using 100 cc. gas samples, 50 cc. samples were used. As a result, values are given in units of parts per million read from a 50 cc. gas sample.

Detection of Stress-Induced Damage to Loblolly Pine

After gas samples were collected, the seedlings were removed from the bags, planted in pots, and placed in a growth room. The development of visual signs of damage to foliage and buds and root growth potential (the number of white roots produced by seedlings) were evaluated after 14 days in the growth room. The results for seedlings from the three nurseries are combined in this presentation. Seedlings were then potted and placed in a growth room to evaluate the development of visual signs of damage to foliage, buds and roots. Root growth potential (the number of white roots produced by seedlings) was evaluated after 14 days in the growth room.

Figure 23A:
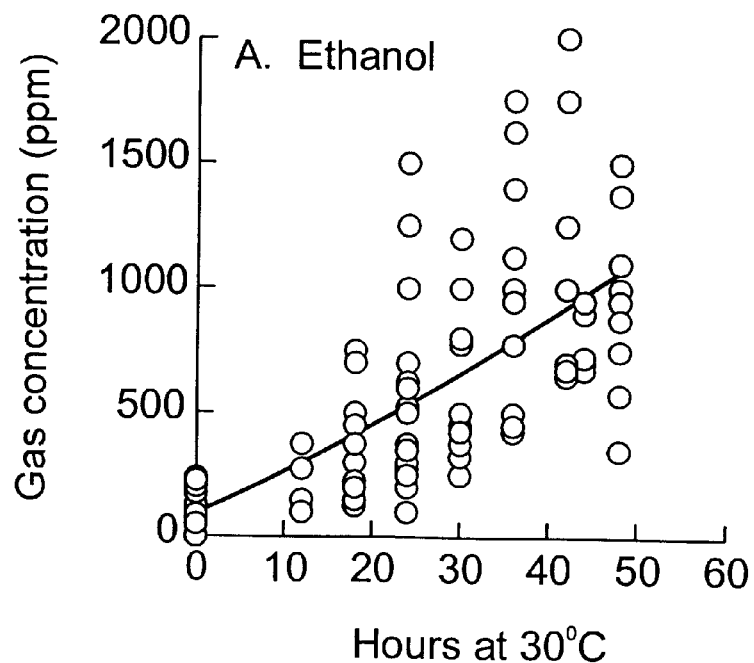
FIG. 23A is a graph showing ethanol gases produced as a result of warm storage at 30° C.
Figure 23B:
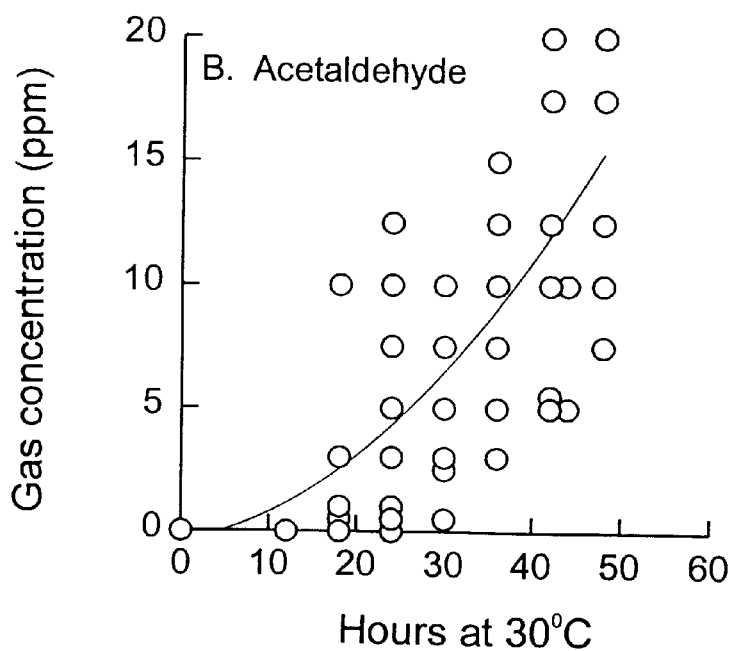
FIG. 23B is a graph showing acetaldehyde gases produced as a result of warm storage at 30° C.
Figure 24A:
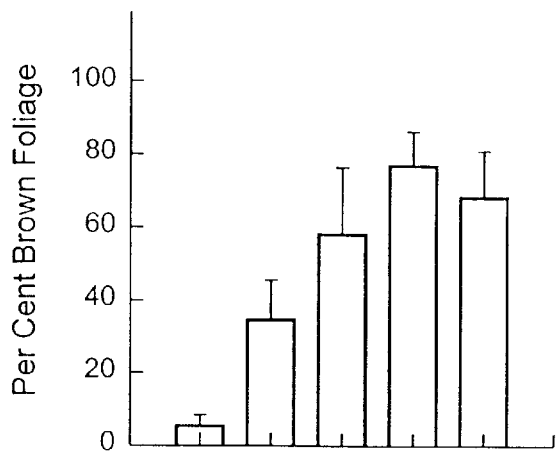
FIGS. 24A–D are graphs showing the relationship between ethanol concentration and seedling quality demonstrated by foliage browning, bud viability, root viability, and white root number.
Figure 24B:
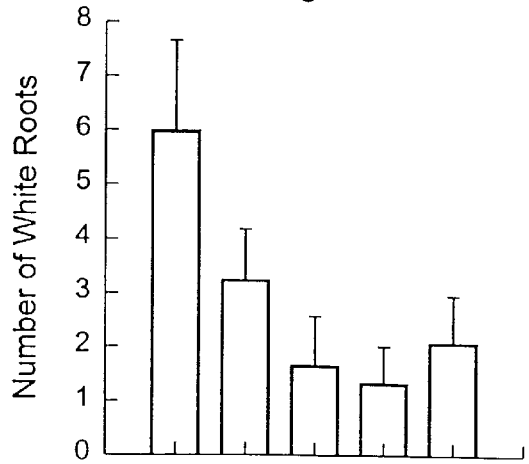
Figure 24C:
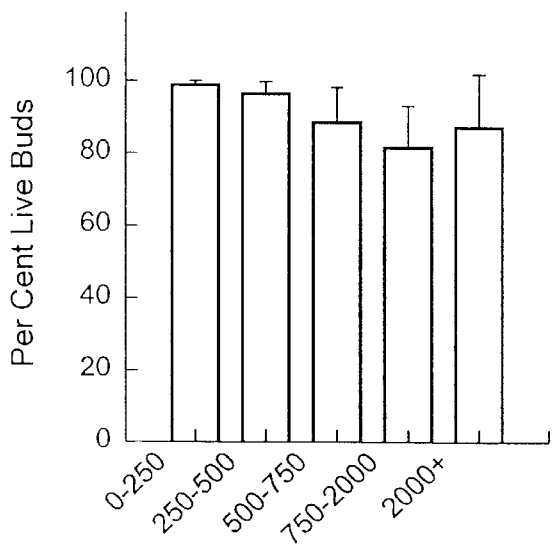
Figure 24D:
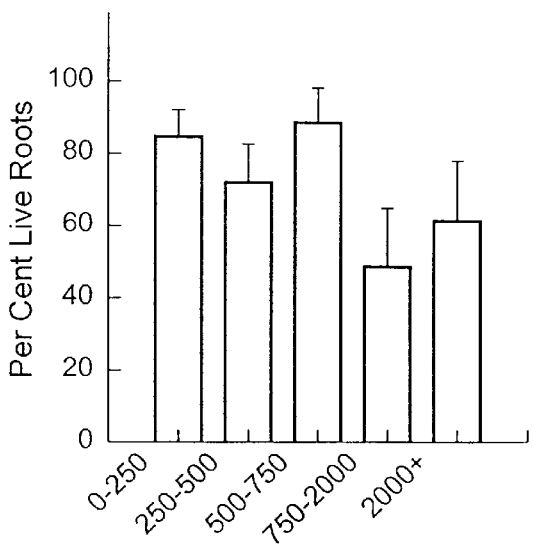
Figure 25A:
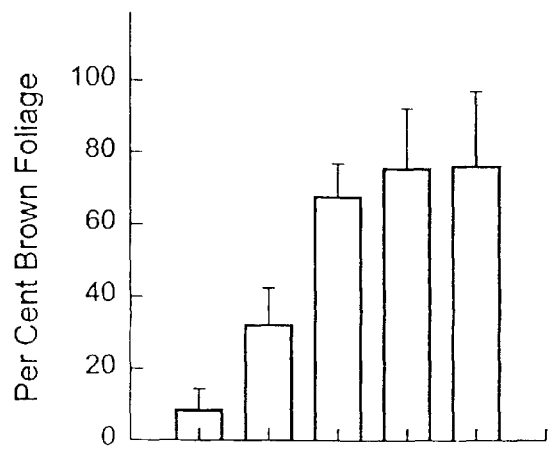
FIGS. 25A–D are graphs showing the relationship between acetaldehyde concentration and seedling quality demonstrated by foliage browning, bud viability, root viability, and white root number.
Figure 25B:
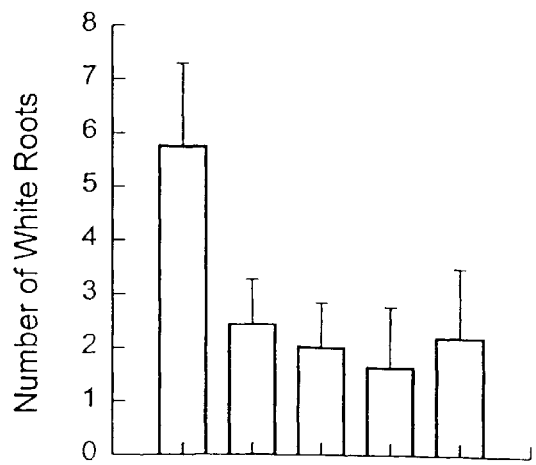
Figure 25C:
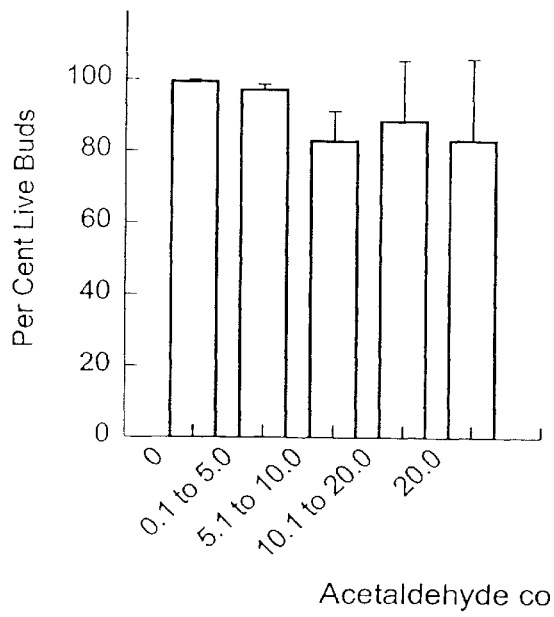
Figure 25D:
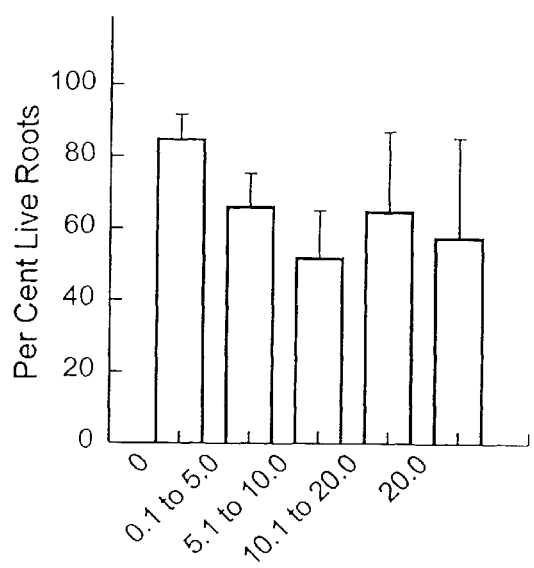

FIG. 23 shows the relationships between duration in warm storage and the production of ethanol and acetaldehyde. Longer durations of storage increased the production of both gases. FIGS. 24A–D illustrates the relationships between different measures of loblolly pine seedling quality and ethanol production. When ethanol values were low (less than about 250 ppm in a 50 cc. gas sample), foliage browning was low and a high number of white roots was produced. When ethanol values were high (i.e., >250 ppm), the severity of foliage browning was greater and fewer white roots were produced. FIGS. 25A–D illustrates similar relationships for acetaldehyde.

These results demonstrate the ability of the invention to detect the quality of loblolly pine seedlings. Threshold concentrations of ethanol and acetaldehyde are identified in Table 6. "Healthy" seedlings (i.e., seedlings without damage) produced no more than a trace of acetaldehyde and less than 250 ppm ethanol. Moderately damaged seedlings (i.e., significantly more damaged than the control groups), had no mortality but suffered visual signs of damage while producing less than 10 ppm acetaldehyde and between 250 and 750 ppm ethanol. Severely damaged seedlings produced more than 10 ppm acetaldehyde and more than 750 ppm ethanol and expressed a high level of foliar damage within a few days and had few viable roots and buds.

Having illustrated and described the principles of the invention in preferred embodiments, it should be appreciated by those skilled in the art that the invention can be modified in arrangement and detail without departure from such principles. We claim all modifications coming within the scope of the following claims. In addition, reference is made herein to various publications and patents, which are hereby incorporated by reference in their entirety.

TABLE 1

| Ethanol concen. (ppm.) | Root Growth Potential (no. of roots > 1 cm) | Foliage viability (% healthy needles) | Terminal bud viability (% viable buds) |
|---|---|---|---|
| Expt. 1 | | | |
| 0 | 48.9a | 88.9a | 100 |
| 200 | 43.5ab | 96.9a | 81.2 |
| 650 | 41.1ab | 90.6ab | 81.2 |
| 900 | 40.4ab | 90.6ab | 93.7 |
| 1100 | 33.0b | 94.7ab | 77.7 |
| 1550 | 24.9c | 68.9bc | 38.8 |
| 1600 | 2.9d | 41.4c | 16.6 |
| 1800 | 7.6d | 39.4c | 0.0 |
| Expt. 2 | | | |
| 300 | 34.4a | 93.8a | 62.5 |
| 450 | 41.3a | 96.1a | 64.7 |
| 1150 | 41.4a | 91.2a | 53.2 |
| 1550 | 36.1a | 86.6a | 50.0 |
| 1600 | 13.6b | 63.1b | 18.7 |
| 2300 | 11.7b | 54.4b | 16.6 |
| Expt. 3 | | | |
| 0 | 41.6a | 86.8ab | 68.6 |
| 450 | 36.4a | 95.0a | 83.3 |
| 500 | 35.4a | 91.6ab | 55.6 |
| 950 | 41.2a | 96.7a | 72.2 |
| 1400 | 33.1a | 87.2b | 38.9 |
| 2100 | 14.6b | 52.5c | 11.1 |
| Expt. 4 | | | |
| 0 | 44.8a | 99.0a | 50.0 |
| 550 | 43.6a | 97.2a | 33.4 |
| 950 | 47.2a | 98.7a | 54.9 |
| 2000 | 7.4b | 11.3b | 0.9 |

Note:
Means followed by a different letter within columns in each experiment differ at g < 0.05. Tests of significance for seedlings attributes were Student-Newman-Keuls test for root growth potential and foilage viability, and $X^2$ test for terminal bud variety.

TABLE 2

| Dependent Variable (x) | Independent Variable (y) | Regression Equation | $R^2$ |
|---|---|---|---|
| Ethanol Concentration | Root Viability | $y = (-7.15 \times 10 - 6)x^2 - (1.31 \times 10 - 3)x + 43.81$ | 0.73 |
| | Bud Viability | $y = (-1.80 \times 10^{-5})x^2 + 0.0127x + 93.51$ | 0.69 |
| | Foliage Viability | $y = (-1.48 \times 10^{-6})x^2 - (3.67 \times 10^{-4})x + 73.26$ | 0.64 |

TABLE 3

White Spruce Ethanol

| | Ethanol Range of concentration (ppm) | Mean viability (%) | Confidence Interval @ 95% (%) |
|---|---|---|---|
| Root Viability | 0–339 ppm | 74.53 | 8.63 |
| | 400–1199 ppm | 20.68 | 10.07 |
| | 1200 + ppm | 0.00 | 0.00 |
| Bud Viability | 0–399 ppm | 90.58 | 5.07 |
| | 400–1199 ppm | 16.43 | 10.49 |
| | 1200 + ppm | 0.00 | 0.00 |
| Foliage Viability | 0–399 ppm | 91.06 | 4.38 |
| | 400–1199 ppm | 33.60 | 12.77 |
| | 1200 + ppm | 10.76 | 11.23 |

TABLE 4

White Spruce Aldehyde

| | Aldehyde Range of concentration (ppm) | Mean viability (%) | Confidence Interval @ 95% (%) |
|---|---|---|---|
| Root Viability | 0–19.8 | 74.24 | 7.16 |
| | 20–29.9 | 55.71 | 9.03 |
| | 30+ | 10.30 | 4.00 |
| Bud Viability | 0–19.9 | 89.84 | 6.90 |
| | 20–29.9 | 47.86 | 30.62 |
| | 30+ | 7.67 | 7.47 |
| Foliage Viability | 0–19.9 | 92.21 | 3.40 |
| | 20–29.9 | 69.14 | 18.60 |
| | 30+ | 21.11 | 10.04 |

TABLE 5

Correlations between root, bud, and foliage viability and methods of estimating plant quality.

| Dependent Variable (x) | Independent Variable (y) | Regression Equation | $R^2$ |
|---|---|---|---|
| Storage Duration | Root Viability | $y = 0.2x^2 - 2.11x + 122.48$ | 0.72 |
| | Bud Viability | $y = 0.03x^2 - 4.16x + 156.21$ | 0.91 |
| | Foliage Viability | $y = 1.48x + 113.71$ | 0.67 |
| Ethanol Concentration | Root Viability | $y = 0.06x + 70.87$ | 0.69 |
| | Bud Viability | $y = 0.07x + 81.42$ | 0.71 |
| | Foliage Viability | $y = 0.06x + 88.39$ | 0.69 |
| Aldehyde Concentration | Root Viability | $y = 1.06x + 68.46$ | 0.64 |
| | Bud Viability | $y = 1.31x + 81.83$ | 0.67 |
| | Foliage Viability | $y = 1.23x + 89.42$ | 0.72 |
| Chlorophyll Fluorescence Quantum Yield | Root Viability | $y = 54.76x^2 + 73.43x + 0.70$ | 0.78 |
| | Bud Viability | $y = 113.39x^2 + 60.15x + 0.66$ | 0.82 |
| | Foliage Viability | $y = 101.21x^2 + 204.16x + 3.4$ | 0.94 |
| Relative Conductivity | Root Viability | $y = 3.17x + 81.04$ | 0.48 |
| | Bud Viability | $y = 3.84x + 96.22$ | 0.48 |
| | Foliage Viability | $y = -3.29x + 99.82$ | 0.46 |

TABLE 6

Estimated threshold levels of ethanol and acetaldehyde associated with changes in loblolly pine seedling quality.

| | Predicted Seedling Quality Level | | |
|---|---|---|---|
| Gas | Healthy | Moderate Damage | Severe Damage |
| Ethanol | <250 ppm | 250 to 750 ppm | >750 ppm |
| Aldehyde | <trace ppm | 0 to 10 ppm | >10 ppm |

We claim:

1. A method of assessing whether a fruit, vegetable, plant, or flower has stress-induced damage, comprising the steps of:
   (a) maintaining a fruit, vegetable, plant, or flower in isolation in a substantially gas tight enclosure to trap gases evolved from the fruit, vegetable, plant or flower;
   (b) measuring a concentration of at least one volatile gas in the trapped gases by contacting the trapped gases with a colorimetric reagent that changes colour on contact with the volatile gas to be measured and;
   (c) assessing whether the fruit, vegetable, plant, or flower has stress-induced damage by comparing the concentration of volatile gas to control concentrations of the volatile gas obtained from at least one control sample having known stress-induced damage or no damage.

2. A method as claimed in claim 1 wherein the fruit, vegetable, plant, or flower has stress-induced damage if it has a concentration of volatile gas higher than a threshold concentration measured in the control sample.

3. A method as claimed in claim 2 wherein the threshold concentration is determined by exposing control samples to different levels of stress to produce samples having different levels of stress-induced damage; quantitatively measuring the concentration of at least one volatile gas produced by the fruit, vegetable, plant, or flower as described in steps (a) and (b); and comparing the concentrations of volatile gas to the stress-induced damage in the controls exposed to the stress to determine the threshold concentration of gas above which an exposed fruit, vegetable, plant, or flower has stress-induced damage.

4. A method of assessing viability or condition of plant tissue, comprising the steps of;
   maintaining plant tissue in isolation in a substantially gas tight enclosure to trap gases evolved from the plant tissue;
   removing a sample of the trapped gases;
   measuring a concentration of at least one volatile gas in the sample by contacting the sample with a colorimetric reagent that changes colour on contact with the volatile gas; and
   assessing viability of the plant tissue by comparing the colour change of the colorimetric reagent to a known standard.

5. A method as claimed in claim 4, wherein the plant tissue is a seed, seedling, leaf, cutting, plant, bulb or tuber.

6. A method as claimed in claim 4, wherein the plant tissue is a fruit, vegetable or flower.

7. A method as claimed in claim 4 wherein the volatile gas is ethanol or an aldehyde.

8. A method of assessing viability of a seedling sample of a genus, species or cultivar of plant, comprising the steps of:
   (a) maintaining the seedling sample in isolation in a substantially gas tight enclosure to trap gases evolved from the seedling sample;
   (b) measuring a concentration of at least one volatile gas in the trapped gases by contacting the trapped gases with a colorimetric reagent that changes colour on contact with the volatile gas to be measured; and
   (c) assessing viability of the seedling by comparing the concentration of volatile gas to control concentrations of the volatile gas obtained from at least one control seedling sample of known viability.

9. A method as claimed in claim 8 wherein the seedling sample is assessed as non-viable when it has a concentration of volatile gas higher than a threshold concentration measured in the control seedling samples.

10. A method as claimed in claim 9 wherein the threshold concentration is determined by:

exposing control seedling samples to different levels of stress to produce exposed seedling samples having quantitatively different levels of viability;

quantitatively measuring the concentration of at least one volatile gas evolved from the exposed seedlings as described in steps (a) and (b);

quantitatively measuring a known indicator of viability of the seedling samples and;

comparing the concentrations of volatile gas to the known indicator of viability of the exposed seedlings to determine the threshold concentration of gas above which viability is affected or the threshold concentration of gas above which the exposed seedlings are non-viable;

this unexpectedly enables the simple, reliable field determination of thresholds of viability concentrations of (various materials) in a simple on-off manner to be used for screening.

11. A method as claimed in claim 10 wherein the known indicator of viability in the exposed seedlings is quantitated based on one or more factors selected from the group consisting of root growth, shoot growth, dormancy of terminal buds and foliage damage.

12. A method as claimed in claim 10 wherein the different levels of viability in the exposed seedlings are quantitated based on one or more factors selected from the group consisting of the number of new roots, dormancy status of terminal bud, foliage damage, length of new terminal shoots, chlorophyll fluorescence and electrolyte leakage.

13. A method as claimed in claim 10 wherein the stress is heat, cold, water deficit or pollution.

14. A method as claimed in claim 13 wherein the volatile gas is ethanol and the colorimetric reagent is potassium dichromate.

15. A method as claimed in claim 8 wherein the plant is a tree.

16. A method as claimed in claim 15 wherein the tree is a white spruce or a black spruce.

17. A method as claimed in claim 16 wherein the volatile gas is ethanol or an aldehyde.

\* \* \* \* \*